US011135384B2

(12) United States Patent
Gale et al.

(10) Patent No.: US 11,135,384 B2
(45) Date of Patent: Oct. 5, 2021

(54) METHOD, APPARATUS AND SYSTEM FOR AUTOMATICALLY CONTROLLING INSPIRED OXYGEN DELIVERY

(71) Applicant: University of Tasmania, Hobart (AU)

(72) Inventors: Timothy John Gale, Hobart (AU); Peter Anderson Dargaville, Hobart (AU)

(73) Assignee: University of Tasmania, Hobart (AU)

(*) Notice: Subject to any disclaimer, the term of this patent is extended or adjusted under 35 U.S.C. 154(b) by 538 days.

(21) Appl. No.: 15/774,946

(22) PCT Filed: Nov. 10, 2016

(86) PCT No.: PCT/AU2016/051077
§ 371 (c)(1),
(2) Date: May 9, 2018

(87) PCT Pub. No.: WO2017/079798
PCT Pub. Date: May 18, 2017

(65) Prior Publication Data
US 2018/0353718 A1 Dec. 13, 2018

(30) Foreign Application Priority Data
Nov. 10, 2015 (AU) .............................. 2015904621

(51) Int. Cl.
*A61M 16/00* (2006.01)
*A61M 16/12* (2006.01)
(Continued)

(52) U.S. Cl.
CPC ........... *A61M 16/026* (2017.08); *A61B 5/083* (2013.01); *A61B 5/0816* (2013.01);
(Continued)

(58) Field of Classification Search
CPC .... A61M 16/00; A61M 16/0003–0012; A61M 16/06–0694; A61M 16/20–209;
(Continued)

(56) References Cited

U.S. PATENT DOCUMENTS 5,365,922 A * 11/1994 Raemer ................ A61B 5/0833
128/202.22
6,186,142 B1 2/2001 Schmidt
(Continued)

FOREIGN PATENT DOCUMENTS

RU 2011135950 3/2013
WO WO 2006/127356 11/2006
(Continued)

OTHER PUBLICATIONS

International Search Report for Application No. PCT/AU2016/051077 dated Jan. 23, 2017 (4 pages).
(Continued)

*Primary Examiner* — Jan Christopher L Merene
*Assistant Examiner* — Ned T Heffner
(74) *Attorney, Agent, or Firm* — Nixon Peabody LLP

(57) ABSTRACT

Provided herein is a method for automatically controlling inspired oxygen delivery, including: receiving signals representing a plurality of input oxygen saturation ($SpO_2$) values for a patient; generating control values based on the input $SpO_2$ values and a target $SpO_2$ value; and generating output inspired oxygen concentration ($FiO_2$) values based on the control values and reference inspired oxygen concentration ($rFiO_2$) values; wherein the control values include: immediate control values, generated based on the input $SpO_2$ values, the target $SpO_2$ value, and an immediate gain coefficient; accumulation control values, generated based on the input $SpO_2$ values, the target $SpO_2$ value, and an accumulation gain coefficient; and predictive control values,
(Continued)

generated based on the input $SpO_2$ values, the target $SpO_2$ value, and a predictive gain coefficient; wherein the immediate gain coefficient is determined based on the $rFiO_2$ value; and wherein a non-linear compensation weighting is applied to the accumulation control value based on a predetermined non-linear relationship between partial pressure of arterial oxygen ($PaO_2$) and $SpO_2$.

22 Claims, 22 Drawing Sheets

(51) Int. Cl.
    *A61B 5/00* (2006.01)
    *A61B 5/083* (2006.01)
    *A61B 5/1455* (2006.01)
    *A61B 5/08* (2006.01)
    *G16H 40/63* (2018.01)
    *G16H 20/40* (2018.01)

(52) U.S. Cl.
    CPC .......... *A61B 5/0826* (2013.01); *A61B 5/0833* (2013.01); *A61B 5/0836* (2013.01); *A61B 5/1455* (2013.01); *A61B 5/14551* (2013.01); *A61B 5/4836* (2013.01); *A61B 5/7275* (2013.01); *A61B 5/7405* (2013.01); *A61B 5/746* (2013.01); *A61M 16/0003* (2014.02); *A61M 16/0051* (2013.01); *A61M 16/12* (2013.01); *G16H 20/40* (2018.01); *G16H 40/63* (2018.01); *A61M 2016/0027* (2013.01); *A61M 2202/0208* (2013.01); *A61M 2205/3327* (2013.01); *A61M 2205/502* (2013.01); *A61M 2205/581* (2013.01); *A61M 2205/583* (2013.01); *A61M 2230/205* (2013.01)

(58) Field of Classification Search
    CPC ....... A61M 2016/0015–0042; A61M 2230/00; A61M 2230/205; A61M 2230/435; A61B 5/00; A61B 5/145; A61B 5/1455; A61B 5/14551; A61B 5/14542
    See application file for complete search history.

(56) References Cited

U.S. PATENT DOCUMENTS

| | | |
|---|---|---|
| 6,325,978 B1 | 12/2001 | Labuda |
| 6,371,114 B1 | 4/2002 | Schmidt |
| 6,532,958 B1 | 3/2003 | Buan |
| 6,561,187 B2 | 5/2003 | Schmidt |
| 6,671,529 B2 | 12/2003 | Claure |
| 7,331,343 B2 | 2/2008 | Schmidt |
| 7,802,571 B2 | 9/2010 | Tehrani |
| 2002/0072659 A1 | 6/2002 | Claure |
| 2010/0186742 A1 | 7/2010 | Sherman |
| 2010/0224192 A1 | 9/2010 | Dixon |
| 2010/0331639 A1 | 12/2010 | O'Reilly |
| 2011/0041849 A1 | 2/2011 | Chen |
| 2011/0067697 A1 | 3/2011 | Lellouche |
| 2012/0090611 A1 | 4/2012 | Graboi |

FOREIGN PATENT DOCUMENTS

| | | |
|---|---|---|
| WO | WO2009120607 | 10/2009 |
| WO | WO 2014/118653 | 8/2014 |

OTHER PUBLICATIONS

Krone, B.; "Modeling and control of Arterial Oxygen Saturation on Permature Infants"; Thesis presented to the Faculty of the Graduate School, University of Missouri—Columbia, Jul. 2011 (84 pages).

Fathabadi, O.S. et al.; "Assessment of Validity and predictability of the Fi02-Sp02 transfer-function in preterm infants"; Physiological Measurement, 2014, pp. 1425-1437 (13 pages).

Morozoff, E.P. et al.; "Evaluation of Three Automatic Oxygen Therapy Control Algorithms on Ventilated Low Birth Weight Neonates"; 31st Annual International Conference on the IEEE EMBS, Sep. 2009, pp. 3079-3082; Abstract only (1 page).

Tehrani, F. T.; "A closed-loop system for control of the fraction of inspired oxygen and the positive end-expiratory pressure in mechanical ventilation"; Computers in Biology and Medicine, 2012, pp. 1150-1156; Abstract only (1 page).

Fathabadi, O. S. et al.; "Binary search for time-constant estimation in first order systems, FiO2-Sp02 case study"; Abstract; The 2013 Biomedical Engineering International Conference (BMEiCON-2013) (3 pages).

Lau, Y. Y. et al.; "Maintaining Optimal Oxygen Saturation in Premature Infants"; Perm J. 2011 Winter; 15(1): e108-e113 (6 pages).

Lin, S.-C. et al.; "Fuzzy oxygen control system for the indirect calorimeter of premature infants"; Journal of Medical Engineering & Technology, vol. 25, 2001—Issue 4; pp. 149-155 (8 pages).

Bhutani, V. et al.; "Adaptive control of inspired oxygen delivery to the neonate"; Pediatr. Pulmonol. (1992); 14: 110-7 (8 pages).

Morozoff, P. et al.; "Closed-loop control of SaO2 in the neonate"; Biomedical Instrumentation & Technology/Association for the Advancement of Medical Instrumentation (1992); 26: 117-123 (7 pages).

Sun, Y. et al.; "Computer-assisted adjustment of inspired oxygen concentration improves control of oxygen saturation in newborn infants requiring mechanical ventilation"; J. Pediatr. (1997); 131: 754-6 (5 pages).

Bolton, D.P.; "Further observations on cost of preventing retrolental fibroplasia"; Lancet 1974;1:445-448 (4 pages).

Silverman, W.A.; "A cautionary tale about supplemental oxygen: the albatross of neonatal medicine"; Pediatrics 2004;113:394-396 (5 pages).

Carlo, W.A. et al.; "Target ranges of oxygen saturation in extremely preterm infants"; N. Engl. J. Med. May 27, 2010; vol. 362, No. 21, pp. 1959-1969 (11 pages).

Stenson, B.J. et al.; "Oxygen saturation and outcomes in preterm infants"; N. Engl. J. Med. May 30, 2013; 368:2094-2104 (11 pages).

Van Zanten, H.A. et al.; "The risk for hyperoxaemia after apnoea, bradycardia and hypoxaemia in preterm infants"; Arch. Dis. Child Fetal Neonatal Ed. 2014; 99: F269-F273 (6 pages).

STOP-ROP Multicenter study group; "Supplemental Therapeutic Oxygen for Prethreshold Retinopathy of Prematurity (STOP-ROP), a randomized, controlled trial. I: primary outcomes"; Pediatrics 2000;105:295-310 (18 pages).

Stenson, B.J. et al.; The twists and turns of neonatal oxygen therapy; Early Hum. Dev. 2012; 88:961-963 (3 pages).

Clarke, a. et al.; "A randomised crossover trial of clinical algorithm for oxygen saturation targeting in preterm infants with frequent desaturation episodes"; Neonatology 2015; 107:130-136 (7 pages).

Claure, N. et al.; "Automated adjustment of inspired oxygen in preterm infants with frequent fluctuations in oxygenation: a pilot clinical trial"; J. Pediatr. 2009; 155:640-645 (8 pages).

Petterson, M.T. et al.; "The effect of motion on pulse oximetry and its clinical significance"; Anesth. Analg. 2007; 105:S78-S84 (7 pages).

Lim, K., et al.; "Lost without trace: oximetry signal dropout in preterm infants"; Arch. Dis. Child Fetal Neonatal Ed. 2015; 10.1136/archdischild-2014-308108 (4 pages).

Rowe, L., et al.; "A simplified method for deriving shunt and reduced VA/Q in infants"; Arch. Dis. Child Fetal Neonatal Ed. 2010; 95:F47-F52 (7 pages).

Jones, J.G. et al.; "Discriminating between the effect of shunt and reduced VA/Q on arterial oxygen saturation is particularly useful in clinical practice"; J. Clin. Monit. Comput. 2000; 16:337-350 (14 pages).

Sapsford, D.J., et al.; "The PIO2 vs. SpO2 diagram: a non-invasive measure of pulmonary oxygen exchange"; Eur. J. Anaesthesiol. 1995; 12:375-386 (12 pages).

(56) References Cited

OTHER PUBLICATIONS

Fathabadi, O.S., et al.; "Characterization of the oxygenation response to inspired oxygen adjustments in preterm infants"; Neonatology 2015; in press (7 pages).
Visioli, A.; "Practical PID control"; London: Springer Verlag, 2006; pp. 1-6 (6 pages).
Schmitt, H.J. et al.; "Accuracy of pulse oximetry in children with cyanotic congenital heart disease"; J. Cardiothorac. Vasc. Anesth. 1993; vol. 7, No. 1, pp. 61-65 (5 pages).
Alderliesten, T. et al.; Perfusion Index in Preterm Infants during the First 3 Days of Life: Reference Values and Relation with Clinical Variables; Neonatology Feb. 25, 2015; 107:258-265 (9 pages).
Isermann, R.; "Digital control systems"; Berlin Heidelberg: Springer, 1989. p. 103 (3 pages).
Lim, K. et al.; "Oxygen Saturation Targeting in Preterm Infants Receiving Continuous Positive Airway Pressure"; J. Pediatr. (Apr. 2014); vol. 164, No. 4, pp. 730-736 (8 pages).
Beddis, I. et al.; "New technique for servo-control of arterial oxygen tension in preterm infants"; Departments of Paediatrics and Neonatal Medicine, and Medical Physics, Hammersmith Hospital, London; Archives of Disease in Childhood, vol. 54, pp. 278-280; 1979 (3 pages).
Beresford, M. et al.; "Twelve-Month Prospective Study of Oxygen Saturation Measurements among Term and Preterm Infants"; Journal of Perinatology, vol. 25, pp. 30-32; 2005 (4 pages).
Claure, N. et al.; "Multicenter Crossover Study of Automated Control of Inspired Oxygen in Ventilated Preterm Infants"; Pediatrics (2011); 127: e76-83 (11 pages).
Claure, N. et al.; "Closed-loop controlled inspired oxygen concentration for mechanically ventilated very low birth weight infants with frequent episodes of hypoxemia"; Pediatrics (2001); 107:1120-4 (7 pages).
Dugdale, R. et al.; "Closed-loop control of the partial pressure of arterial oxygen in neonates"; Clin. Phys. Physiol. Meas. (1988); vol. 9, No. 4, pp. 291-305 (16 pages).
Hagadorn, J. et al.; "Achieved Versus Intended Pulse Oximeter Saturation in Infants Born Less Than 28 Weeks' Gestation: The AVIOx Study"; Pediatrics (2006); 118: 1574-82 (11 pages).
Hallenberger, A. et al.; "Closed-Loop Automatic Oxygen Control (CLAC) in Preterm Infants: A Randomized Controlled Trial"; Pediatrics (2014); 133: e379-85 (9 pages).
Laptook, A.R. et al.; "Pulse oximetry in very low birth weight infants: can oxygen saturation be maintained in the desired range?"; J. Perinatol. (2006); 26: 337-41 (6 pages).
Severinghaus, J.; "Simple, accurate equations for human blood O2 dissociation computations"; J. Appl. Physiol. Respir. Environ. Exerc. Physiol. 1979; 46(3):599-602 (2 pages).
Tehrani, F.T. et al.; "A feedback controller for supplemental oxygen treatment of newborn infants: a simulation study"; Med. Eng. Phys., vol. 16, pp. 329-333; Jul. 1994 (5 pages).
Urschitz, M. et al.; "Automatic Control of the Inspired Oxygen Fraction in Preterm Infants a Randomized Crossover Trial"; Am. J. Respir. Crit. Care Med. (2004); vol. 170: 1095-1100 (6 pages).
Van Kaam, A. et al.; "Automated versus Manual Oxygen Control with Different Saturation Targets and Modes of Respiratory Support in Preterm Infants"; J. Pediatr. (2015); vol. 167, No. 3, pp. 545-550 (8 pages).
Waitz, M. et al.; "Effects of Automated Adjustment of the Inspired Oxygen on Fluctuations of Arterial and Regional Cerebral Tissue Oxygenation in Preterm Infants with Frequent Desaturations"; J. Pediatr. (2015); 166: 240-244 (6 pages).
Zapata, J. et al.; "A randomised controlled trial of an automated oxygen delivery algorithm for preterm neonates receiving supplemental oxygen without mechanical ventilation"; Acta Paediatr. (2014); 103: 928-33 (6 pages).
Saugstad, O. et al.; "Optimal oxygenation of extremely low birth weight infants: a meta-analysis and systematic review of the oxygen saturation target studies"; Neonatology 2014; 105:55-63 (9 pages).
Flynn, J.T. et al.; "A cohort study of transcutaneous oxygen tension and the incidence and severity of retinopathy of prematurity"; N. Engl. J. Med.; Apr. 16, 1992; vol. 326, No. 16, pp. 1050-1054 (5 pages).
Poets, C.F. et al.; "Association between intermittent hypoxemia or bradycardia and late death or disability in extremely preterm infants"; JAMA 2015; 314(6):595-603. (Aug. 11, 2015) (9 pages).
Lal, M. et al.; "Automated control of inspired oxygen in ventilated preterm infants: crossover physiological study"; Acta Paediatr. 2015; 104:1084-89 (Jul. 21, 2015) (6 pages).
Wilinska, M. et al.; "Quicker response results in better SpO2 control—a comparison of 3 FiO2-titration strategies in ventilated preterm infants"; Ann. Agric. Environ. Med. 2015; vol. 22, No. 4, pp. 708-712 (5 pages).
Claure, N. et al.; "Automated closed loop control of inspired oxygen concentration"; Respir. Care, Jan. 2013; vol. 58, No. 1, pp. 151-161 (11 pages).
Hütten, M.C., et al.; "Fully automated predictive intelligent control of oxygenation (PRICO) in resuscitation and ventilation of preterm lambs"; Pediatr. Res. 2015; vol. 78, No. 6, pp. 657-663 (Aug. 31, 2015) (7 pages).
Bolivar, J.M., et al.; "Mechanisms for episodes of hypoxemia in preterm infants undergoing mechanical ventilation"; J. Pediatr. Nov. 1995; 127:767-73 (7 pages).
Di Fiore, J.M., et al.; "Low oxygen saturation target range is associated with increased incidence of intermittent hypoxemia"; J. Pediatr. 2012; vol. 161, No. 6, pp. 1047-1052 (7 pages).
Tehrani, F., et al.; "Closed-loop control if the inspired fraction of oxygen in mechanical ventilation"; J. Clin. Monit. Comput. 2002; vol. 17, No. 6, pp. 367-376 (10 pages).
Quine, D., et al.; "Non-invasive measurement of reduced ventilation: perfusion ratio and shunt in infants with bronchopulmonary dysplasia: a physiological definition of the disease"; Arch. Dis. Child Fetal Neonatal Ed. 2006; 91:F409-14 (7 pages).
Lockwood, G.G., et al.; "Evaluation of a computer program for non-invasive determination of pulmonary shunt and ventilation-perfusion mismatch"; J. Clin. Monit. Comput. 2014; 28:581-90 (10 pages).
Poets, C.F., et al.; Potential role of intrapulmonary shunting in the genesis of hypoxemic episodes in infants and young children; Pediatrics; Sep. 1992; vol. 90, No. 3, pp. 385-391 (9 pages).
Hummler, H., et al.; "Automated adjustments of inspired fraction of oxygen to avoid hypoxemia and hyperoxemia in neonates—a systematic review on clinical studies"; Klin. Padiatr. 2014; 226: 204-210 (8 pages).
Julious, S.A., et al.; "Estimating sample sizes for continuous, binary, and ordinal outcomes in paired comparisons: practical hints"; J. Biopharm. Stat. 1999; 9(2):241-51 (12 pages).
Chow, L.C., et al.; "Can changes in clinical practice decrease the incidence of severe retinopathy of prematurity in very low birth weight infants?"; Pediatrics. 2003; vol. 111, No. 2, pp. 339-345 (9 pages).
Di Fiore, J.M., et al.; "The relationship between patterns of intermittent hypoxia and retinopathy of prematurity in preterm infants"; Pediatr. Res. 2012; vol. 72, No. 6, pp. 606-612 (7 pages).
Claure, N., et al.; "Role of automation in neonatal respiratory support"; J. Perinat. Med. 2013; 41(1): 115-118 (4 pages).
Collins, P., et al.; "Apparatus for the servocontrol of arterial oxygen tension in preterm infants"; Med. Biol. Eng. Comput. 17 (4) (1979) 449-452 (4 pages).
Claure, N.; Automated regulation of inspired oxygen in preterm infants: oxygenation stability and clinician workload; Anesth. Analg. 2007; 105(6):S37-S41 (5 pages).
Bancalari, E. et al.; "Control of oxygenation during mechanical ventilation in the premature infant"; Clin. Perinatol. 2012; 39(3): 563-572 (10 pages).
Claure, N., et al.; "Closed-loop control of inspired oxygen in premature infants"; Semin. Fetal Neonatal Med.; Jun. 2015; 20(3): 198-204 (7 pages).
Claure, N., et al.; "Oxygen saturation targeting by automatic control of inspired oxygen in premature infants"; NeoReviews 16(7):e406-e412 (Jul. 2015) (9 pages).

(56) References Cited

OTHER PUBLICATIONS

Morozoff, E.P., et al.; "Automatic control of blood oxygen saturation in premature infants"; in: Second IEEE Conference on Control Applications, IEEE, Sep. 13-16, 1993; pp. 415-419 (6 pages).
Miksch, S., et al.; "Abstracting steady qualitative descriptions over time from noisy, high-frequency data"; vol. 1620, in: Book Section Artificial Intelligence in Medicine: Joint European Conference on Artificial Intelligence in Medicine and Medical Decision Making, Lecture Notes in Computer Science, Springer, 1999, pp. 281-290 (10 pages).
Seyfang, S., et al.; "Using time-oriented data abstraction methods to optimize oxygen supply for neonates"; vol. 2101, in: Book Section Artificial Intelligence in Medicine: 8thConference on Artificial Intelligence in Medicine in Europe, Lecture Notes in Computer Science, Springer, 2001, pp. 217-226 (10 pages).
Y. Sun, et al.; "Fuzzy logic assisted control of inspired oxygen in ventilated newborn infants"; in: Proceedings of the Annual Symposium on Computer Application in Medical Care, 1994, pp. 757-761 (5 pages).
Morozoff, E.P.; "Modelling and Fuzzy Logic Control of Neonatal Oxygen Therapy" (Thesis), Theses (School of Engineering Science)/ Simon Fraser University, Dec. 1996 (190 pages).
Lopez, J. et al.; "Auto-mixer: equipment for the reduction of risks associated with inadequate oxygen supply"; Ing. Investig. vol. 34, No. 1, pp. 60-65; 2014 (12 pages).
Tehrani, F.; "A control system for oxygen therapy of premature infants"; in: Proceedings of the 23rd Annual International Conference of the IEEE Engineering in Medicine and Biology Society, vol. 2, IEEE, 2001, pp. 2059-2062 (4 pages).
Sano, M., et al.; "Adaptive control of arterial oxygen pressure of newborn infants under incubator oxygen treatments"; IEE Proc. D Control Theory Appl. vol. 132, No. 5, pp. 205-211.; Sep. 1985 (7 pages).
Taube, J.C., et al.; "Criteria for an adaptive fractional inspired oxygen controller"; in: Proceedings of the Symposium on the Engineering of Computer-Based Medical Systems, IEEE, 1988, pp. 129-132 (4 pages).
Taube, J., et al.; "Automatic control of neonatal fractional inspired oxygen"; in: Proceedings of the Annual International Conference of the IEEE Engineering in Medicine and Biology Society, vol. 13, IEEE, 1991, pp. 2176-2177 (2 pages).
Stephan, S.; "SpO2 Controller"; retrieved from http://stephan-gmbh.com (5 pages).
Keim, T., et al.; "Modeling and feedback control of inspired oxygen for premature infants"; in: ASME Oct. 31-Nov. 2, 2011 Dynamic Systems and Control Conference; pp. 501-508 (8 pages).
Skogestad, S., et al.; "Multivariable Feedback Control: Analysis and Design"; John Wiley, London, 2005 (585 pages).
Hay, W., et al.; "Neonatal pulse oximetry: accuracy and reliability"; Pediatrics vol. 83, No. 5, pp. 717-722; May 5, 1989 (8 pages).
Castillo, A., et al.; "Pulse oxygen saturation levels and arterial oxygen tension values in newborns receiving oxygen therapy in the neonatal intensive care unit: is 85% to 93% an acceptable range?"; Pediatrics, Vo. 121, No. 5, pp. 882-889; 2008 (10 pages).
Poets, C.F.; "Apnea of prematurity: what can observational studies tell us about pathophysiology?"; Sleep Med. 11 (7) (2010) 701-707 (7 pages).
Pantalitschka, T., et al.; "Randomised crossover trial of four nasal respiratory support systems for apnoea of prematurity in very low birthweight infants"; Arch. Dis. Child Fetal Neonatal Ed. 94 (4) (2009) F245-F248 (5 pages).

Poets, C.F., et al.; "Noninvasive monitoring of oxygenation in infants and children: practical considerations and areas of concern"; Pediatrics, vol. 93, No. 5, pp. 737-746; May 1994 (12 pages).
Dawson, J., et al.; "The precision and accuracy of Nellcor and Masimo oximeters at low oxygen"; Arch. Dis. Child Fetal Neonatal. Ed. 99 (4) (2014) F278-F281 (4 pages).
Mazeika, G.; "Respiratory Inductance Plethysmography: An Introduction"; 2007, pp. 1-13, www.pro-tech.com; (13 pages).
Banovcin, P., et al.; "Pressure sensor plethysmography a method for assessment of respiratory motion in children"; Eur. Respir. J. 8 (1) (1995) 167-171 (5 pages).
Khalidi, A.L., et al.; "Respiration rate monitoring methods: a review"; Pediatr. Pulmonol. 46 (6) (2011) 523-529 (7 pages).
Lee, Y., et al.; "Monitoring and analysis of respiratory patterns using microwave Doppler radar"; IEEE J. Transl. Eng. Health Med. 2 (2014) 1-12 (12 pages).
Tan, K.S., et al.; "Real-time vision based respiration monitoring system, 7th International Symposium on Communication Systems Networks and Digital Signal Processing"; IEEE (2010) 770-774 (5 pages).
Abbas, A.K., et al.; "Neonatal non-contact respiratory monitoring based on real-time infrared thermography"; Biomed. Eng. Online 10 (2011) 93 (17 pages).
Schmidt, B., et al.; "Effects of targeting higher vs. lower arterial oxygen saturations on death or disability in extremely preterm infants: a randomized clinical trial"; JAMA, vol. 309, No. 20, pp. 2111-2120; May 22-29, 2013 (10 pages).
Askie, L.M.; "Optimal oxygen saturations in preterm infants: a moving target"; Curr. Opin. Pediatr. 25 (2) (2013) 188-192 (5 pages).
Bashambu, M. T., et al.; "Evidence for oxygen use in preterm infants"; Acta Paediatr. 101 (s464) (2012) 29-33 (5 pages).
Bancalari, E., et al.; "Oxygenation targets and outcomes in premature infants";. JAMA, vol. 309, No. 20, pp. 2161-2162; May 22-29, 2013 (2 pages).
Sola, S.G., et al.; "Safe oxygen saturation targeting and monitoring in preterm infants: can we avoid hypoxia and hyperoxia?"; Acta Paediatr. 103 (10) (2014)1009-1018 (10 pages).
Wilinska, M., et al.; "Automated FiO2-SpO2control system in Neonates requiring respiratorysupport: a comparison of a standard to a narrow SpO2control range"; BMC Pediatr. 14 (1) (2014) 130 (5 pages).
Aoyagi, T., et al.; "Multiwavelengthpulse oximetry: theory for the future"; Anesth. Analg., vol. 105, No. 6, pp. S53-S58; Dec. 2007 (6 pages).
Li, K., et al.; "A wireless reflectance pulse oximeter with digital baselinecontrol for unfiltered photoplethysmograms"; IEEE Trans. Biomed. Circuits Syst., vol. 6, No. 3, pp. 269-278; Jun. 2012 (10 pages).
Li, K., et al.; Onboard tagging for real-time qualityassessment of photoplethysmograms acquired by a wireless reflectance pulseoximeter; IEEE Trans. Biomed. Circuits Syst., vol. 6, No. 1, pp. 54-63; Feb. 2012 (10 pages).
Venema, B., et al.; "Advances in reflective oxygen saturation monitoring with a novel in-ear sensor system: results of a human hypoxia study"; IEEE Trans. Biomed. Eng., vol. 59, No. 7, pp. 2003-2010; Jul. 2012 (8 pages).
Venema, B., et al.; "Robustness, specificity, and reliability of an in-ear pulse oximetric sensor in surgical patients"; IEEE J. Biomed. Health Inform., vol. 18, No. 4, pp. 1178-1185; Jul. 2014 (8 pages).

\* cited by examiner

METHOD, APPARATUS AND SYSTEM FOR AUTOMATICALLY CONTROLLING INSPIRED OXYGEN DELIVERY

CROSS-REFERENCE TO RELATED APPLICATIONS

This application is a U.S. National Stage of International Application No. PCT/AU2016/051077, filed Nov. 10, 2016, which claims priority to and the benefit of Australian No. Application No. 2015904621, filed Nov. 10, 2015, each of which is incorporated by reference in its entirety.

TECHNICAL FIELD

The present invention generally relates to a method, an apparatus and a system for automatically controlling inspired oxygen delivery, e.g., a method, an apparatus and a system for automatically controlling inspired oxygen concentration to maintain oxygen saturation in a target range.

BACKGROUND

Supplemental oxygen therapy can be used for a variety of purposes in both chronic and acute patient care. For example, it plays a pivotal role in management of newborn infants with respiratory dysfunction. For preterm infants, studies have shown that there is a connection between unremitting hypoxia and an increase in mortality. Further, it has also been observed that excess oxygen delivery is associated with adverse outcomes, in particular retinopathy of prematurity. Hence, there is a need to continuously adjust the fraction of inspired oxygen ($FiO_2$) to maintain oxygen saturation ($SpO_2$) in an acceptable target range so as to avoid the extremes of oxygenation. The response of $SpO_2$ to changes in $FiO_2$ is referred to as "system gain", where the "system" is the patient.

Currently, striking a balance in delivering oxygen to preterm infants is largely in the hands of bedside caregivers, who manually adjust $FiO_2$ in an effort to maintain oxygen saturation $SpO_2$ in a target range. Unfortunately such manual control of $FiO_2$ is imprecise, with infants spending a considerable amount of time with $SpO_2$ outside the target ranges.

Automated adjustment of $FiO_2$ may afford more time in the target range than manual control, and considerably reduce the proportion of iatrogenic hyperoxia and severe hypoxia. However, there are significant challenges in applying automation of oxygen delivery to preterm infants with lung dysfunction. A first challenge is to improve the effectiveness in $SpO_2$ targeting and to avoid time in and episodes of, hypoxia and hyperoxia. A second challenge for automated control of oxygen delivery is that the main determinants of oxygenation are intermingled with endless variety in premature infants, and contribute fundamentally different responses to changes in $FiO_2$, thus an automated controller with a uniform and unchanging response to a given $SpO_2$ perturbation may be incapable of serving the needs of all individuals. A third challenge is that system gain may change over time.

It is desired to address or ameliorate one or more disadvantages or limitations associated with the prior art, or to at least provide a useful alternative.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

SUMMARY

In accordance with an aspect of the present invention there is provided a method for automatically controlling inspired oxygen delivery, including:
  receiving signals representing a plurality of input oxygen saturation ($SpO_2$) values for a patient;
  generating control values based on the input $SpO_2$ values and a target $SpO_2$ value; and
  generating output inspired oxygen concentration ($FiO_2$) values based on the control values and reference inspired oxygen concentration ($rFiO_2$) values;
  wherein the control values include:
    immediate control values, generated based on the input $SpO_2$ values, the target $SpO_2$ value, and an immediate gain coefficient;
    accumulation control values, generated based on the input $SpO_2$ values, the target $SpO_2$ value, and an accumulation gain coefficient; and
    predictive control values, generated based on the input $SpO_2$ values, the target $SpO_2$ value, and a predictive gain coefficient;
  wherein the immediate control valves are determined based on the $rFiO_2$ value; and
  wherein a non-linear compensation weighting is applied to the accumulation control value based on a predetermined non-linear relationship between partial pressure of arterial oxygen ($PaO_2$) and $SpO_2$.

In accordance with another aspect of the present invention there is provided an apparatus for automatically controlling inspired oxygen delivery, including:
  an input unit, receiving signals representing a plurality of input oxygen saturation ($SpO_2$) values for a patient;
  a memory, recording the received input $SpO_2$ values;
  a controller, determining output inspired oxygen concentration ($FiO_2$) values based on the input $SpO_2$ values; and
  an output unit, outputting the determined output $FiO_2$ values;
  wherein the controller:
    generates control values based on the input $SpO_2$ values and a target $SpO_2$ value; and
    generates the output inspired oxygen concentration ($FiO_2$) values based on the control values and reference inspired oxygen concentration ($rFiO_2$) values;
  wherein the control values include:
    immediate control values, generated based on the input $SpO_2$ values, the target $SpO_2$ value, and an immediate gain coefficient;
    accumulation control values, generated based on the input $SpO_2$ values, the target $SpO_2$ value, and an accumulation gain coefficient; and
    predictive control values, generated based on the input $SpO_2$ values, the target $SpO_2$ value, and a predictive gain coefficient;
  wherein the immediate control valves are determined based on the $rFiO_2$ value; and
  wherein a non-linear compensation weighting is applied to the accumulation control value based on a predetermined non-linear relationship between partial pressure of arterial oxygen ($PaO_2$) and $SpO_2$.

In accordance with another aspect of the present invention there is provided a system for automatically controlling inspired oxygen delivery, including:
one or a plurality of oxygen saturation monitoring devices, and one or a plurality of inspired oxygen control devices;
a controlling device; and
a network, enabling communication between the one or a plurality of oxygen saturation monitoring devices and the controlling device, and communication between the one or a plurality of inspired oxygen control devices and the controlling device,
wherein the controlling device controls inspired oxygen delivery by:
receiving signals representing a plurality of input oxygen saturation ($SpO_2$) values for a patient from each of the one or a plurality of oxygen saturation monitoring devices through the network;
generating control values based on the input $SpO_2$ values and a target $SpO_2$ value;
generating output inspired oxygen concentration ($FiO_2$) values based on the control values and reference inspired oxygen concentration ($rFiO_2$) values;
sending the determined output $FiO_2$ values to a corresponding inspired oxygen control device through the network;
wherein the control values include:
immediate control values, generated based on the input $SpO_2$ values, the target $SpO_2$ value, and an immediate gain coefficient;
accumulation control values, generated based on the input $SpO_2$ values, the target $SpO_2$ value, and an accumulation gain coefficient; and
predictive control values, generated based on the input $SpO_2$ values, the target $SpO_2$ value, and a predictive gain coefficient;
wherein the immediate control valves are determined based on the $rFiO_2$ value; and
wherein a non-linear compensation weighting is applied to the accumulation control value based on a predetermined non-linear relationship between partial pressure of arterial oxygen ($PaO_2$) and $SpO_2$.

In accordance with an aspect of the present invention there is provided a method for automatically controlling inspired oxygen delivery, including:
receiving signals representing a plurality of input oxygen saturation ($SpO_2$) values for a patient;
generating control values based on the input $SpO_2$ values and a target $SpO_2$ value; and
generating output inspired oxygen concentration ($FiO_2$) values based on the control values and reference inspired oxygen concentration ($rFiO_2$) values;
wherein the control values include:
immediate control values, generated based on the input $SpO_2$ values, the target $SpO_2$ value, and an immediate gain coefficient;
accumulation control values, generated based on the input $SpO_2$ values, the target $SpO_2$ value, and an accumulation gain coefficient; and
predictive control values, generated based on the input $SpO_2$ values, the target $SpO_2$ value, and a predictive gain coefficient.

BRIEF DESCRIPTION OF THE DRAWINGS

Some embodiments of the present invention are hereinafter described, by way of example only, with reference to the accompanying drawings, in which.

DETAILED DESCRIPTION

Described herein is an inspired oxygen delivery system 100 which performs a method of automatically controlling inspired oxygen delivery to a patient (e.g., a human infant).

The described system (and method) may provide one or more advantages compared to pre-existing systems and methods. First, the described system may efficiently target the desired $SpO_2$ range and avoid the extremes of oxygenation. Second, the described system may respond rapidly to $SpO_2$ deviations, e.g., due to vicissitudes of the V/Q ratio and shunt within the lung. Third, the described system may compensate for non-linearities in the $PaO_2$-$SpO_2$ relationship (where $PaO_2$ means partial pressure of arterial oxygen—e.g., $PaO_2$ changing by only 1-2 mm Hg for each 1% step change in SpO$_2$ on the linear portion of the sigmoid curve, but by more than 20 mm Hg further towards the asymptote). Fourth, the described system can respond differently for different individuals to compensate for individuals' variable SpO$_2$ responses to FiO$_2$ adjustments, corresponding to different individuals' mixes of shift in the FiO$_2$-SpO$_2$ curve (where a rightward shift corresponds to a decreasing ventilation-perfusion (V/Q) ratio) and shunt (the proportion or fraction of blood pumped to the body without any oxygen added to it within the lungs). Fifth, the described system may adjust its gain based on performance metrics.

Figure 1:
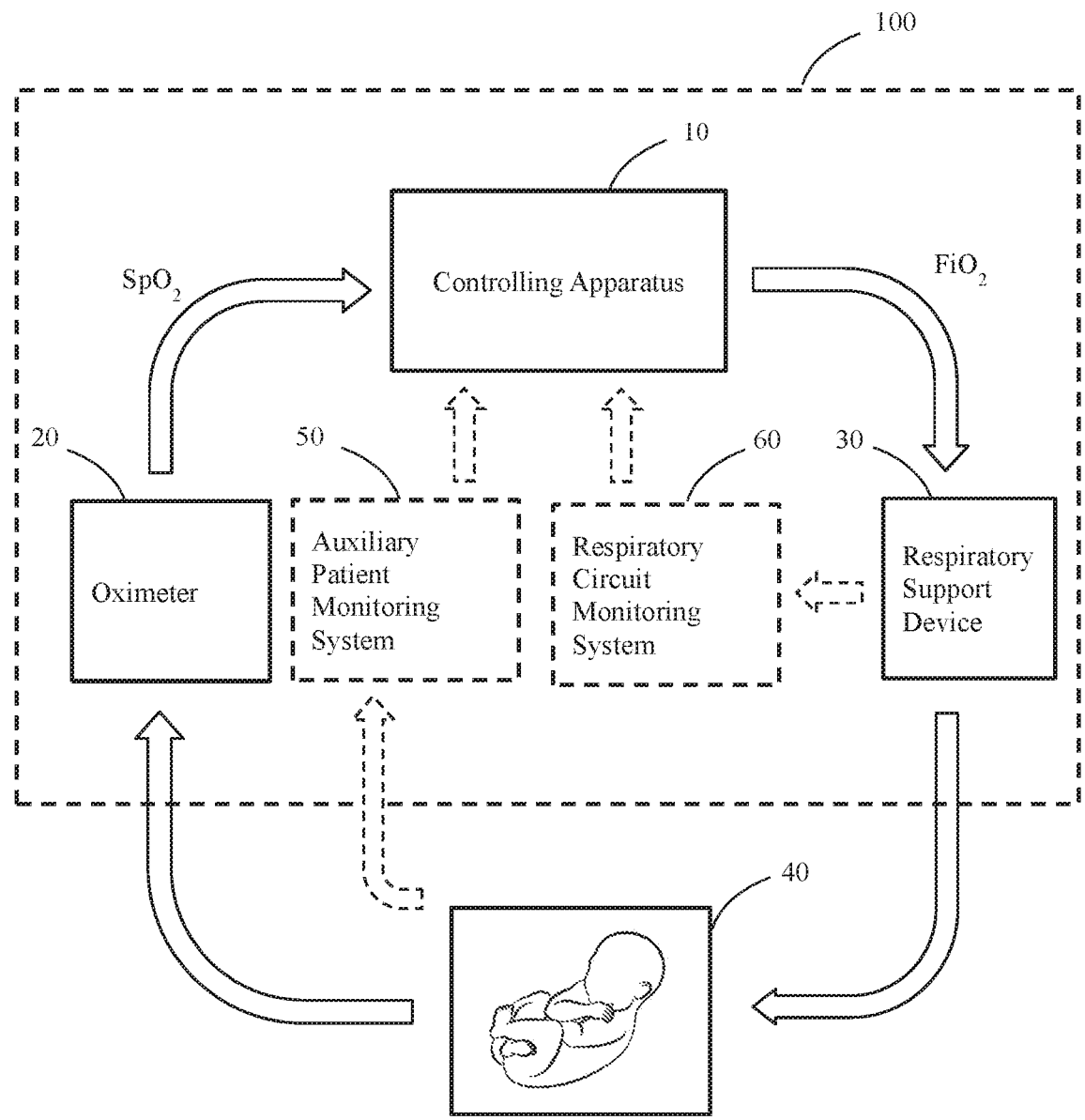
FIG. 1 is a block diagram of an inspired oxygen delivery system.

As shown in FIG. 1, the system 100 includes a controlling apparatus 10, an oximeter 20 and a respiratory support device 30.

The controlling apparatus 10 is configured for automatically controlling inspired oxygen delivery.

The oximeter 20 measures arterial oxygen saturation (SpO$_2$) of a patient 40, and sends an output signal representing SpO$_2$ values to the controlling apparatus 10. The SpO$_2$ value represented by the output signal of the oximeter 20 is also referred to as an "input SpO$_2$ value" from the perspective of the controlling apparatus 10.

The oximeter 20 can have an analogue or digital data output.

Based on the input SpO$_2$ values from the oximeter 20, the controlling apparatus 10 determines an output inspired oxygen concentration (FiO$_2$) value, and outputs a FiO$_2$ signal representing the determined output FiO$_2$ value.

The output FiO$_2$ signal from the controlling apparatus 10 is transmitted to the respiratory support device 30. The respiratory support device 30 is a system capable of responding to an FiO$_2$ input, i.e., the respiratory support system can receive and execute a desired value of FiO$_2$. The respiratory support device 30 can be in the form of an air-oxygen blender, a mechanical ventilator, a continuous positive airway pressure (CPAP) driver, or a flow generator for high flow nasal cannula support or low flow oxygen delivery.

The respiratory support device 30 delivers the blended gas (the fractionally inspired oxygen with the determined FiO$_2$) to the patient 40. The inspired oxygen delivery system 100 may further include an auxiliary patient monitoring system 50, and a respiratory circuit monitoring system 60.

The auxiliary patient monitoring system 50 monitors the patient 40 and outputs signals representing the patient's condition. The auxiliary patient monitoring system 50 may include monitoring devices in the form of a cardiorespiratory monitor or a respiration monitor.

The respiratory circuit monitoring system 60 monitors the output of the respiratory support device 30, i.e., the fraction of inspired oxygen to be delivered to the patient. It outputs signals representing the monitoring results. The respiratory circuit monitoring system 60 may include devices in the form of an oxygen analyser and additionally a pressure transducer.

The outputs from the auxiliary patient monitoring system 50 and the respiratory circuit monitoring system 60 are transmitted to the controlling apparatus 10. The controlling apparatus 10 may determine the output FiO$_2$ value based on the input SpO$_2$ and the signals transmitted from the auxiliary patient monitoring system 50 and the respiratory circuit monitoring system 60.

Figure 2:
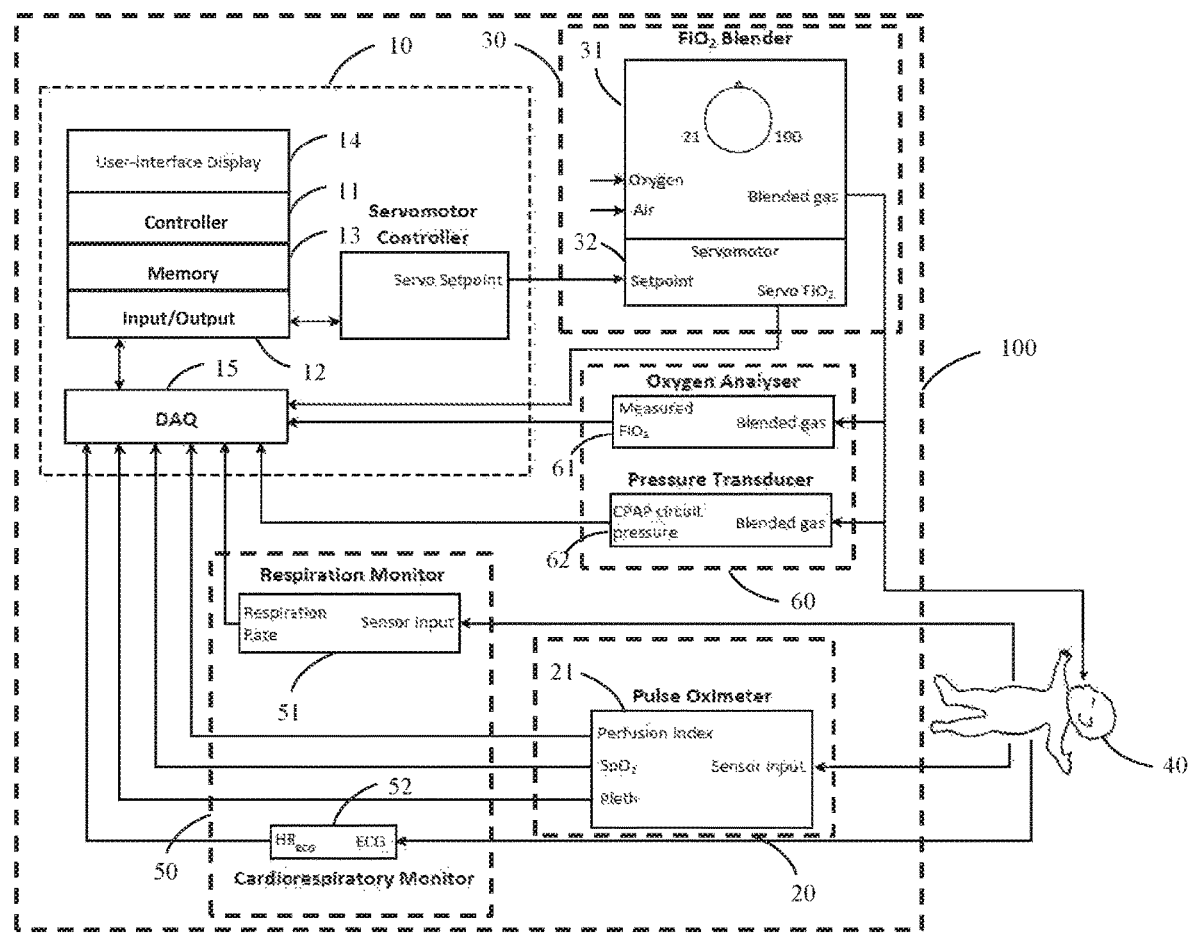
FIG. 2 is a block diagram of components in the inspired oxygen delivery system.

As shown in FIG. 2, the controlling apparatus 10 may be a stand-alone device. The controlling apparatus 10 may include: a controller 11, which determines the output FiO$_2$ value based on the input SpO$_2$ values; and an input/output interface 12, which receives signals representing input SpO$_2$ values and outputs signals representing the determined output FiO$_2$ values. The input/output interface 12 may also received inputs from the auxiliary patient monitoring system 50 and/or the respiratory circuit monitoring system 60.

The controller 11 is in the form of an electronic control apparatus, including one or more digital microcontrollers or microprocessors that perform or execute steps of the method described herein. The controller 11 may include one or more application-specific integrated circuits and/or field-programmable gate arrays that are configured to perform the method steps.

The controlling apparatus 10 may further include a memory 13 which records the received input SpO$_2$ values. The memory 13 may store machine-readable instructions that define the method steps described herein, and are read and executed by the controller 11 to perform one or more of the method steps.

The controlling apparatus 10 may also include a user-interface display 14, which displays a user interface showing various information to a user (e.g., a bedside caregiver) and receives instructions inputted by the user through the user-interface. The received user inputs are transmitted to the controller 11.

The controlling apparatus 10 may further include a data acquisition device (DAQ) 15, which acquires signals/data transmitted from other components of the system 100.

The oximeter 20 may include a pulse oximeter 21. The pulse oximeter 21 measures SpO$_2$ of a patient 40, and sends an output signal representing SpO$_2$ values to the controlling apparatus 10. The pulse oximeter 21 may further measure: (1) a perfusion index, being a metric of oximetry waveform pulsatility, with low values potentially associated with spurious SpO$_2$ values; and (2) a SpO$_2$ plethysmographic waveform ("Pleth"). An output signal representing the perfusion index and an output signal representing a SpO$_2$ plethysmographic waveform are sent to the controlling apparatus 10 from the pulse oximeter 21. The pulse oximeter 21 may further measure a heart rate derived from the SpO$_2$ plethysmographic waveform (HR$_{pleth}$) and send it to the controlling apparatus 10.

The respiratory support device 30 may include an air-oxygen blender 31. From the controlling apparatus 10, a signal representing the determined output FiO$_2$ value may be routed to a servomotor 32 custom-mounted on the air-oxygen blender 31, which allows automatic rotation of the blender FiO$_2$ selection dial via a ringed gearing mechanism. The servomotor 32 and the gearing system may have sufficient torque and precision to allow small adjustments to FiO$_2$ (e.g., minimum±0.5%) to be made accurately and repeatedly. The servomotor 32 may also have a low holding torque such that the blender dial can still be turned manually; such manual intervention may be detected by a position sensor and resulted in a switch to a manual mode in which FiO$_2$ was no longer under automated control.

At the beginning of the automatic control of FiO$_2$, the servomotor calibration may be checked and if necessary altered. The servomotor calibration may also be checked and/or altered periodically during prolonged usage if necessary.

The controlling apparatus 10 may confirm that changes in the output FiO$_2$ value are executed correctly by the servomotor 32, using feedback signals from the servomotor 32 of the position of the FiO$_2$ selector dial (servo FiO$_2$).

As shown in FIG. 2, the auxiliary patient monitoring system 50 may include a respiration monitor 51 and a cardiorespiratory monitor 52. The respiration monitor 51 monitors the respiration of the patient 40 and outputs a signal representing a respiration rate of the patient 40. The cardiorespiratory monitor 52 monitors the electrocardiogram (ECG) of the patient 40 and outputs a signal representing a heart rate of the patient 40 derived from the electrocardiographic monitoring ($HR_{ecg}$). Outputs from the respiration monitor 51 and the cardiorespiratory monitor 52 are transmitted to the controlling apparatus 10.

The respiratory circuit monitoring system 60 may include an oxygen analyser 61 and a pressure transducer 62. The oxygen analyser 61 monitors the output of the air-oxygen blender 31, i.e., the blended gas to be delivered to the patient 40, and outputs a signal representing the measured $FiO_2$ to the controlling apparatus 10. The pressure transducer 62 transduces a pressure in the inspiratory limb of the CPAP circuit, and outputs a signal representing the CPAP circuit pressure to the controlling apparatus 10.

Confirmation that changes in the output $FiO_2$ value sent from the controlling apparatus 10 are executed correctly by the automated air-oxygen blender 31 may also be based on measurement of output $FiO_2$ from the air-oxygen blender 31, using the oxygen analyser 61. Information from the oxygen analyser 61 (measured $FiO_2$) may be digitised from an analogue signal, and may further be offset by a selected flow-time delay (which can be 5 seconds or any other suitable values, and can be selected or determined at the time of system set-up) to compensate for the time for gas flow and equilibration downstream from the blender.

Based on these input signals from the oximeter 20, the auxiliary patient monitoring system 50 and the inspired oxygen monitoring system 60, the controlling apparatus 10 determines the output $FiO_2$ value.

Inputs from the oximeter 20, the auxiliary patient monitoring system 50 and the respiratory circuit monitoring system 60 other than the input $SpO_2$ are referred to as "additional inputs". As described hereinbefore, the additional inputs may include measured $FiO_2$, CPAP circuit pressure, respiration rate, perfusion index, pleth waveform, $HR_{pleth}$, and $HR_{ecg}$.

The controlling apparatus 10 may further include an alarm unit, controlled by the controller 11, for triggering an audible and/or visible alarm. For example, in the event of either servo $FiO_2$ or measured $FiO_2$ deviating from the output $FiO_2$ value beyond tolerance limits (1 and 2%, respectively), an alarm may be triggered. In one example, a high level alarm and a change to manual mode may occur for deviations of 5 and 10%, respectively.

Further, alternatively, the controlling apparatus 10 may not be a stand-alone device, but mounted or integrated in another device. For example, the controlling apparatus 10 may be integrated in the oximeter 20, or integrated in the respiratory support device 30.

As described in further detail hereinafter, the controller 11 may include a core component in the form of a feedback controller that is adapted and configured for automated oxygen control for the preterm infant. The feedback controller includes mechanical, digital and/or electronic circuits to generate output control signals based on input control signals, and internal control values (also referred to as "terms") in the feedback controller. The internal control values may include a summation of:

(a) an immediate control value that adjusts the output based on the current value of the input;
(b) an accumulation control value that adjusts the output based on previous or past values of the input; and
(c) a predictive control value that adjusts the output based on predicted future values of the input.

The method for automatically controlling inspired oxygen delivery includes:

(a) receiving signals representing a plurality of input oxygen saturation ($SpO_2$) values for a patient;
(b) generating control values based on the input $SpO_2$ values and a target $SpO_2$ value; and
(c) generating output inspired oxygen concentration ($FiO_2$) values based on the control values and reference inspired oxygen concentration ($rFiO_2$) values.

The control value may include an immediate control value associated with a comparison of the current input $SpO_2$ value and the target $SpO_2$ value. The immediate control value may be generated based on the input $SpO_2$ values, the target $SpO_2$ value, and an immediate gain coefficient.

The control value may further include an accumulation control value generated based on an accumulation relationship between the input $SpO_2$ values and the target $SpO_2$ value. The accumulation relationship between the input $SpO_2$ values and the target $SpO_2$ value may be an accumulation of differences between the input $SpO_2$ values and the target $SpO_2$ value. The accumulation control value may be generated based on the input $SpO_2$ values, the target $SpO_2$ value, and adjusted by an accumulation gain coefficient.

The control value may further include generating a predictive control value generated based on a predictive relationship between the input $SpO_2$ values and the target $SpO_2$ value. The predictive relationship may be a time derivative of differences between the input $SpO_2$ values and the target $SpO_2$ value. The predictive control value may be generated based on the input $SpO_2$ values, the target $SpO_2$ value, and a predictive gain coefficient.

The feedback controller generates the control value based on the immediate control value, the accumulation control value and the predictive control value, and the $rFiO_2$ value, and determines the output $FiO_2$ value.

In the feedback controller, an error (e) is defined as the deviation of the process signal from a set-point. The feedback controller may be a proportional-integral-derivative (PID) controller.

The PID feedback controller may be enhanced by a number of methods. A measure of severity of lung dysfunction may be obtained periodically by automated assessment of current oxygen requirements. The enhancements of the immediate control value may include modulation based on severity of lung dysfunction, error attenuation while within the target range and error capping during hypoxia. The enhancements of the accumulation control value may include integrand magnitude capping, compensation for the non-linear $PaO_2$-$SpO_2$ relationship, and inhibition of integrand increase in room air.

For the PID feedback controller, the value of the manipulated signal output at each moment is proportional to the error, its integral and its derivative, with a different multiplying coefficient in each case, i.e., the immediate gain coefficient, the accumulation gain coefficient, and the predictive gain coefficient (referred to as $K_p$, $K_i$, $K_d$ respectively). For the PID feedback controller, the immediate control value may also be referred to as a "proportional term"; the accumulation control value may also be referred to as an "integral term"; and the predictive control value may also be referred to as a "derivative term", the three of which may be referred to as "PID terms".

In the method for automatically controlling inspired oxygen delivery as described herein, the immediate control value may be generated by multiplying an error value associated with the difference between the current input $SpO_2$ value and the target $SpO_2$ value) by an immediate gain coefficient. The error value may be the error (e), i.e., generated by determining the difference between the current input SpO$_2$ value and the target SpO$_2$ value. Alternatively, the error value may be generated by other suitable mathematical methods that compare the current input SpO$_2$ value with the target SpO$_2$ value.

For the PID controller, the numerical difference between the incoming value for SpO$_2$ (assuming a valid signal) and the midpoint of the selected target range (e.g., target range 91-95%, mid-point 93%) may be used as the error (e).

Further, the accumulation control value may be generated by multiplying the accumulation of differences between the input SpO$_2$ values and the target SpO$_2$ values by an accumulation gain coefficient. For example, the accumulation control value may be generated by multiplying a summation of the error values by the accumulation gain coefficient for digital signals, or by multiplying an integral of the error values by the accumulation gain coefficient for analog signals. Alternatively, the accumulation control value may be generated by other suitable mathematical methods that result in the accumulation relationship between the input SpO$_2$ values and the target SpO$_2$ value.

For the PID controller, the integrand ($\int e\, d\tau$) may be the sum or integral of all errors (subject to constraints outlined hereinafter); the integral term in PID control lends the advantage of overcoming steady state error.

Further, the predictive control value may be generated by multiplying the difference divided by the time between successive error values (for digital signals) or derivative (for analog signals) of the error values (i.e., differences between the input SpO$_2$ values and the target SpO$_2$ values) by a predictive gain coefficient. Alternatively, the predictive control value may be generated by other suitable mathematical methods that result in the predictive relationship between the input SpO$_2$ values and the target SpO$_2$ value.

For the PID controller, the derivative $$\left(\frac{de}{dt}\right)$$

may be the SpO$_2$ slope by linear regression over the previous 5 seconds, and in PID control gives a prediction of future error.

For example, the sum of each of the PID terms may be represented as $\Delta$FiO$_2$ (as shown in the Equation 1 hereinafter).

As previously described, the output FiO$_2$ value (the FiO$_2$ to be delivered to the patient) may be determined based on the control value and a reference inspired oxygen concentration (rFiO$_2$) value.

In some embodiments, the output FiO$_2$ values may be the sum of the corresponding control value and the corresponding rFiO$_2$ value, i.e., as shown in Equation 2.

For example, FiO$_2$ may be the sum of $\Delta$FiO$_2$ and rFiO$_2$ (as shown in the Equation 2 hereinafter). In addition, FiO$_2$ may be rounded to ±0.5% and coerced to a value between 21 and 100%, i.e., any value under 21% is rounded up to 21% and any value over 100% is rounded down to 100%.

$$\Delta\text{FiO}_2 = K_p \cdot e + K_i \cdot \int e\, d\tau + K_d \cdot \frac{de}{dt} \quad \text{(Equation 1)}$$

$$\text{Set FiO}_2 = \Delta\text{FiO}_2 + r\text{FiO}_2 \quad \text{(Equation 2)}$$

The rFiO$_2$ value may represent the current baseline oxygen requirement, which indicates the severity of lung dysfunction of the patient. It may be a predetermined value or a value range, or may be selected by user's input. For example, the rFiO$_2$ value may be predetermined as a number between 21% and 60%, or any other suitable number up to 100%. The rFiO$_2$ value may have an initial value and be modified repeatedly over time, as described in further detail hereinafter. The time period for repeating the determination may be fixed (e.g., any period from 30 minutes to 2 hours) or may alternatively be indefinite. In this way, it is possible to detect and respond to the gradual changes in basal oxygen requirement that occur in subjects with respiratory dysfunction.

In some embodiments, the immediate gain coefficient has an initial value selected to be between −2 and −0.2, e.g., −1.

In some embodiments, the accumulation gain coefficient has an initial value selected to be between −0.25 and −0.005, e.g., −0.0125.

In some embodiments, the predictive gain coefficient has an initial value selected to be between −2 and −0.25, e.g., −1.

Each of the values of $K_p$, $K_i$ and $K_d$ may be determined based on predetermined reference values or a value range. For example, $K_p$, $K_i$ and $K_d$ may be determined based on reference values or value ranges derived from simulation studies using data from preterm infants. Values for each of the coefficients may be negative, meaning that the PID terms act in concert to correct the error. Exemplary value ranges for the coefficients may be: $K_p$ −2 to −0.2; $K_i$ −0.25 to −0.005; $K_d$ −2 to −0.25, for example, Kp=−1, Ki=−0.0125, and Kd=−1. As described in further detail hereinafter, the standing value for $K_p$ may be modified depending on the severity of lung dysfunction, and may further be refined through a self-tuning process during the automatic control, e.g., refined once every 30 to 60 minutes (or any other suitable time period which is sufficient for a proper assessment, e.g., more than 10 minutes and less than 120 minutes).

In some embodiments, the immediate control values may be modified.

In some embodiments, the method may further include:
  determining the target SpO$_2$ value based on a target SpO$_2$ range;
  wherein when the current input SpO$_2$ value is within the target SpO$_2$ range, an attenuator is applied to the immediate gain coefficient, and
  wherein the attenuator is generated based on the current input SpO$_2$ value and a midpoint of the target SpO$_2$ range.

The attenuator may be a fractional multiplier that is proportional to difference between the current input SpO$_2$ value and the midpoint of the target SpO$_2$ range.

Further, when the current input SpO$_2$ value is lower than the target SpO$_2$ value, the error value associated with the difference between the current input SpO$_2$ value and the target SpO$_2$ value may be capped at a selected maximum difference.

For the PID control, the determination of the proportional term may be modified when the input SpO$_2$ value is within the target SpO$_2$ range.

The system 100 may target the mid-point of the target range, defining any deviation from this value as an error (e). In recognition that SpO$_2$ values elsewhere within the target range are acceptable, errors related to deviation from the mid-point of the target range may be reduced with a fractional multiplier $K_{pfm}$ proportional to the distance from the mid-point (target range attenuation). For example, for a target range with a span of ±2 from the midpoint (e.g., 91-95%), for |e|=1 a fractional multiplier $K_{pfm}$ of 0.25 may be applied to $K_p$, and for |e|=2 a fractional multiplier $K_{pfm}$ of 0.5 may be applied.

Further, given the relative imprecision of $SpO_2$ monitoring at values less than 80%, negative error may be capped, e.g., at 15% for determination of the proportional term.

In some embodiments, the accumulation control values may be modified.

In some embodiments, a non-linear compensation weighting may be applied to the accumulation control value based on a non-linear, predetermined relationship between partial pressure of arterial oxygen ($PaO_2$) and $SpO_2$.

Further, the accumulation control values may be modified to cap the control value at a selected maximum control value.

For the PID control, the integral term may be modified.

In recognition that the integral term progressively increments $FiO_2$ in the event of unremitting hypoxia, limits may be set on the magnitude of the integrand which limit the maximum $\Delta FiO_2$ that can be output from the PID controller to a value set by the user (which can be ±30 to 40%, i.e., 30 to 40% above or below $rFiO_2$). In hyperoxia (i.e., $SpO_2$ above the target range when in supplemental oxygen), which can follow a hypoxic event as an "overshoot", the error at high $SpO_2$ values may not be proportional to the likely deviation of $PaO_2$ from an acceptable value (i.e., the non-linear $PaO_2$-$SpO_2$ relationship). For this reason, for as long as the integrand remains negative (i.e., tending to increase $\Delta FiO_2$), an error multiplier may be applied to positive errors proportional to relevant $\Delta PaO_2$ values. In one embodiment, the corrected error is added to the integrand with each iteration whilst the integrand remains negative. The error multipliers may be those in Table 1.

TABLE 1

Error multipliers for positive $SpO_2$ errors

| | $SpO_2$ value | | | | | | | | |
|---|---|---|---|---|---|---|---|---|---|
| | 92% | 93% | 94% | 95% | 96% | 97% | 98% | 99% | 100% |
| Error multiplier | 1.2 | 1.4 | 1.7 | 2.2 | 2.9 | 4.4 | 7.9 | 20.1 | 50 |

The error multipliers may have the effect of rapidly increasing negative integrand back towards zero, and thus mitigating overshoot.

Further, in some embodiments, generating the accumulation control values may include:

inhibiting increases in the accumulation control values when: (i) a current output $FiO_2$ value is at room air level, and (ii) a current input $SpO_2$ value is above the target $SpO_2$ value.

Once the integrand is positive (i.e., tending to reduce $\Delta FiO_2$), further positive errors may be added to the integrand only while set $FiO_2$ remains above room air (21%). When in room air (i.e., $FiO_2$=21%), sequential values of $SpO_2$ above the target range may no longer be considered to represent unremitting hyperoxia, and the positive errors may not be added to the integrand, i.e., these positive error values are nulled or zeroed. This may avoid a build-up of positive integrand that would delay an appropriate response from the integral term to the next episode of hypoxia.

In some embodiments, the predictive control values may be modified.

In some embodiments, the predictive control values may be nullified if the input $SpO_2$ values have been above a selected $SpO_2$ threshold for the entirety of the negative $SpO_2$ slope determination period.

For the PID control, the derivative term may be modified. For example, the derivative term may be modified during hyperoxia.

In some embodiments, negative $SpO_2$ slope may be nullified (e.g., rendered=0) if all of the latest 5 $SpO_2$ values are above the set-point (a hyperoxia event). Upward pressure on $\Delta FiO_2$ by the derivative term may thus be avoided in hyperoxia.

Figure 3:
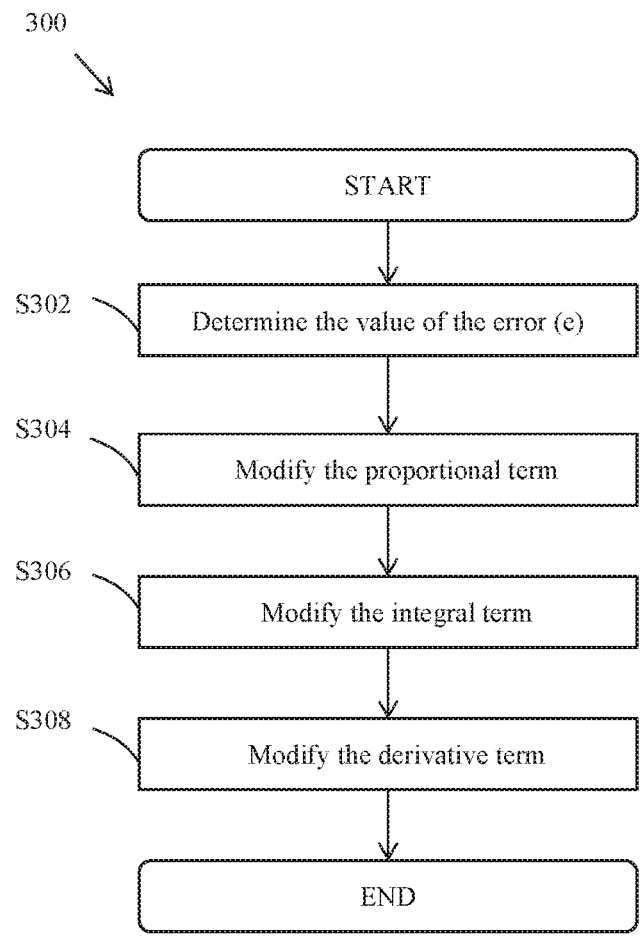
FIG. 3 is a flow chart depicting a process of generating PID terms, i.e., generating the proportional term, the integral term and the derivative term.

FIG. 3 illustrates a process 300 performed by the controller 11 of generating the proportional term, the integral term and the derivative term, including the modifications as described hereinbefore.

As shown in FIG. 3, in S302, a value of the error (e) is determined as the numerical difference between an input $SpO_2$ value and a target $SpO_2$ value (e.g., the midpoint of the selected target range), as shown in Equation 3 below.

$$e = SpO_2 - SpO_2 \text{ target} \quad \text{(Equation 3)}$$

Next, in S304, the proportional term is modified, using the following steps:

(a) Select a value for the fractional multiplier $K_{pfm}$ based on the value of the error:

If |e|<=1 (i.e., the error is smaller than or equal to 25% of the target range, and thus the input $SpO_2$ value is within the target range and close to the target $SpO_2$ value), $K_{pfm}$=0.25;

else if |e|<=2 (i.e., the error is bigger than 25% of the target range but smaller than or equal to 50% of the target range, and thus the input $SpO_2$ value is within the target range while not close to the target $SpO_2$ value), $K_{pfm}$=0.5;

else (i.e., the error is bigger than 50% of the target range, and thus the input $SpO_2$ value is outside the target range) $K_{pfm}$=1.

(b) Adjusting $K_{pfm}$ based on CPAP Circuit Pressure and respiratory rate:

If (CPAP Circuit Pressure=low), $K_{pfm}$=2*$K_{pfm}$ (i.e., reduction in circuit pressure leads to doubling of $K_{pfm}$);

else if (respiratory pause for 5 to 15 sec), $K_{pfm}$=2*$K_{pfm}$ for 30 seconds (i.e., a respiratory pause results in a doubling of $K_{pfm}$ for 30 seconds).

(c) Apply proportional term error capping during hypoxia:

If e>−15% (i.e., the patient is in hypoxia), the proportional error $e_p$=−15% (i.e., cap the proportional term error);

else $e_p$=e.

(d) Calculate the proportional term:

$$\text{Proportional Term} = P(t) = K_{pfm} * K_p * e_p.$$

After the modification of the proportional term, the logic moves to S306 to modify the integral term, using the following steps:

(a) Determination of a non-linear compensation multiplier ($K_s$) based on a non-linear, predetermined relationship, which can be predetermined using known relationships between blood oxygen level and high values of $SpO_2$: (including those described by the Severinghaus equation):

If the previous integral term I(t−1)<0 (i.e., the integrand remained negative) and e>0 (i.e., $SpO_2$ is above the target range),
then
if $SpO_2$=92, $K_s$=1.2;
else if $SpO_2$=93, $K_s$=1.4;
else if $SpO_2$=94, $K_s$=1.7;
else if $SpO_2$=95, $K_s$=2.2;
else if $SpO_2$=96, $K_s$=2.9;
else if $SpO_2$=97, $K_s$=4.4;
else if $SpO_2$=98, $K_s$=7.9;
else if $SpO_2$=99, $K_s$=20.1;
else if $SpO_2$=100, $K_s$=50;
else $K_s$=1

(i.e., apply the non-linear compensation multiplier to positive errors proportional to relevant $\Delta PaO_2$ values).

(b) Inhibition of integrand increase in room air:
If $FiO_2$=21% (i.e., in room air) and e>0, dI=0 (i.e., further positive error is not added to the integrand);

else $dI=K_i*K_s*e$.

(c) Determine the value of integral term:

Integral Term=$I(t)=I(t-1)+dI$.

(d) Integrand magnitude capping:

If $|I(t)|>|\Delta FiO_2 max/K_i|, I(t)=(sign)*(\Delta FiO_2 max/K_i)$ (i.e., cap the value of integral term based on selected $\Delta FiO_2 max$ value).

After the modification of the integral term, the derivative term is then modified in S308 using the following steps:
(a) Evaluate Derivative Term:
Derivative Term=$D(t)=K_d*de/dt$, where de/dt is determined by linear regression over 5 seconds.
(b) Nullify for negative slope and hyperoxia:
If de/dt<0 and ($SpO_2(t)$>$SpO_2$ target) and
($SpO_2(t-1)$>$SpO_2$ target) ($SpO_2(t-2)$>$SpO_2$ target) and
($SpO_2(t-3)$>$SpO_2$ target) and ($SpO_2(t-4)$>$SpO_2$ target)
(i.e., all of the latest 5 $SpO_2$ values are above the set-point),
D(t)=0 (i.e., negative $SpO_2$ slope is nullified).

Further, the control value may be generated further based on the $rFiO_2$ value.

In some embodiments, the immediate control value (the proportional term) is determined further based on the $rFiO_2$ value.

The immediate control value (the proportional term) is modified by a modification value determined from the $rFiO_2$ value. The modification value may be determined using a monotonic relationship with $rFiO_2$, i.e., based on a monotonic function. For example, $K_p$ may be modified from a predetermined initial reference value or from its current value by a value determined from the $rFiO_2$ value. This modification value increases the effective value of the immediate control value for increasing $rFiO_2$, e.g., with a scaling factor proportional to the severity of lung dysfunction as indicated by the current $rFiO_2$. For example, the standing value of $K_p$ may be multiplied by a factor in the range 0.5 to 1.5 for $rFiO_2$ in a corresponding range 21% to 60% (e.g., for $rFiO_2$ 21%, scaling factor may be 0.5, for $rFiO_2$ 40%, the scaling factor may be 1.0, and the scaling factor can vary linearly from 0.5 to 1.5 proportional to the $rFiO_2$ varying from 21% to 60%). Alternatively, the scaling factor can be implemented as an equivalent modification value that modifies the immediate control value. Adaptation of $K_p$ in this way may compensate for an inverse proportional relationship between gain and severity of lung disease.

Further, the method may further include:
receiving the signals representing the plurality of input $SpO_2$ values during a performance analysis time period;
generating a performance evaluation result based on the input $SpO_2$ values received during the performance analysis time period; and
generating the control value based on the performance evaluation result.

Further, the immediate gain coefficient is modified based on a performance evaluation result.

In some embodiments, the value of $K_p$ may be modified repeatedly during automated control of inspired oxygen delivery: an analysis of the performance of the automatic control of inspired oxygen delivery may be carried out periodically, based on the input $SpO_2$ values received over a performance analysis time period and generating a performance evaluation result, and the value of $K_p$ may be modified based on the performance evaluation result.

In some embodiments, the performance evaluation result may be generated based on at least one of: a hypoxic time duration in which the input $SpO_2$ values in the performance analysis time period were in a hypoxic range, and a hyperoxic time duration in which the input $SpO_2$ values in the performance analysis time period were in a hyperoxic range.

Further, in some embodiments, the performance evaluation result is generated based on a ratio of the hyperoxic time duration to the hypoxic time duration.

Further, in some embodiments, the method may further include:
determining the target $SpO_2$ value based on a target $SpO_2$ range;
wherein the performance evaluation result is generated based on at least one of:
a target time duration in which the input $SpO_2$ values in the performance analysis time period were in the target $SpO_2$ range, and
an eupoxic time duration in which the input $SpO_2$ values in the performance analysis time period were in an eupoxic range, wherein the eupoxic range is a range in which the input $SpO_2$ values were in the target $SpO_2$ range, or above the target $SpO_2$ range in room air.

The performance analysis time period may be a fixed time period, e.g., predetermined or set by the user. The performance analysis time period may be 60 minutes, such that the analysis is performed based on the $SpO_2$ data recorded in the last 60 minutes before the analysis. Alternatively, the performance analysis time period may be a variable time period (e.g., any time period between 30 minutes and 2 hours), based on the result of the analysis, or instructions inputted by the user.

The analysis may be performed on a regular basis. For example, the analysis may be performed once every 30 minutes. The analysis may also be performed continuously, or performed once after each of a certain interval, which may be any suitable time period up to 2 hours. The frequency of the analysis may also be set by the user.

The analysis may be based on the response to all hypoxic events in the time window, starting at hypoxia onset ($SpO_2$<85%), and continuing for a certain period (any selected suitable time period between 2 and 10 minutes) beyond its resolution.

The total time of hypoxia ($SpO_2$ 80-84%) and severe hypoxia ($SpO_2$<80%), as well as the duration of subsequent SpO$_2$ overshoot into hyperoxia (97-98%) and severe hyperoxia (99-100%) when receiving oxygen, may be quantified, as described hereinafter with reference to FIG. 4.

From these data, a weighted performance coefficient may be derived as the ratio of time in hyperoxia to time in hypoxia, value of which <1 and >1 may indicate an underpowered and overpowered K$_p$, respectively. The current value of K$_p$ may be altered by up to ±10% each 30 min as a result of this analysis.

Further, proportions of time in which SpO$_2$ was in the target range and in an eupoxic range (SpO$_2$ in target range, or above target range in room air) may be calculated, as well as the occurrence of hypoxia and hyperoxia in oxygen.

In some embodiments, an alarm may be triggered when the performance evaluation result fails to meet certain conditions, including the controller output is substantially below the minimum requirement for proportion of eupoxia, which can be adjusted by the user, and set in the range 50 to 80%.

Figure 4:
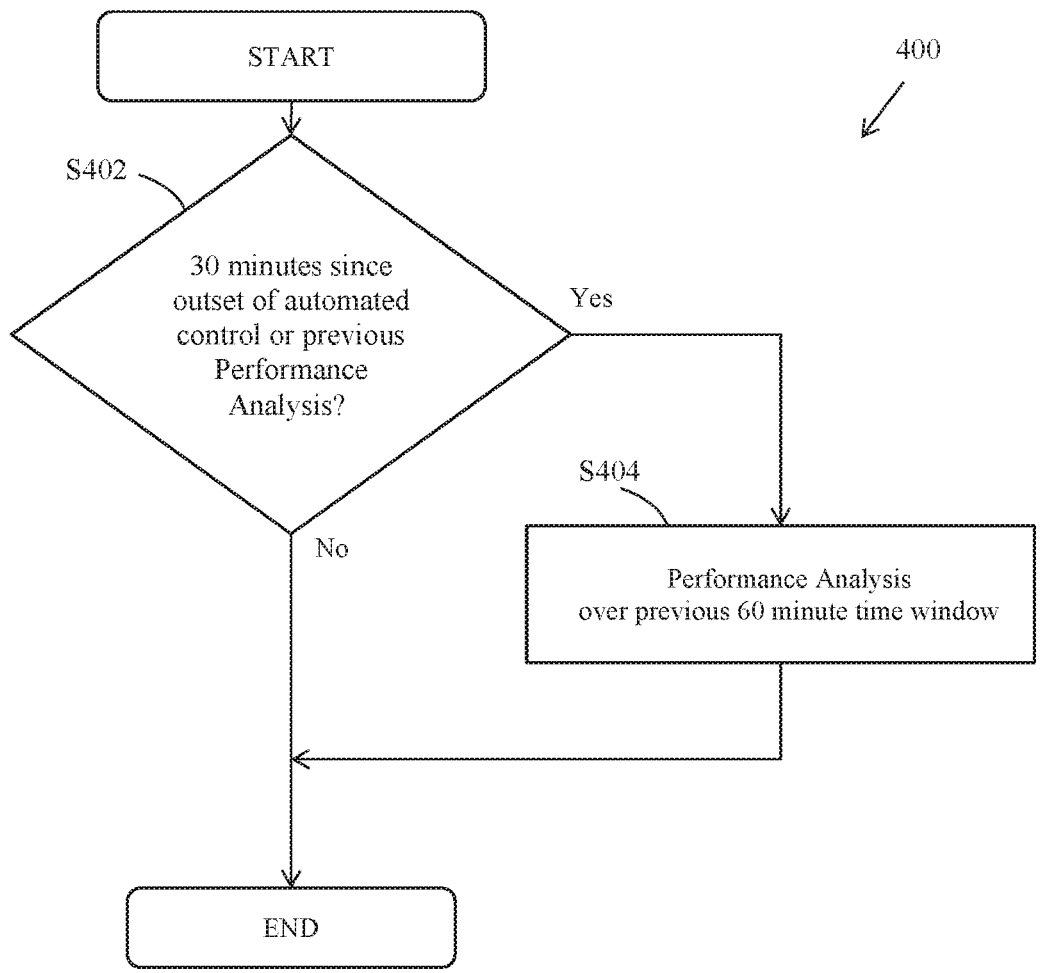
FIG. 4 is a flow chart depicting a process of modifying $K_p$ based on the performance evaluation result.

FIG. 4 illustrates a process 400 performed by the controller 11 of modifying K$_p$ based on the performance evaluation result as described hereinbefore.

As shown in FIG. 4, in S402, the process 400 determines whether 30 minutes have elapsed since outset of automated control or previous Performance Analysis.

If the result of determination is no, the process 400 ends. If it is determined that 30 minutes have elapsed, the process 400 moves to S404 to execute a performance analysis based on the performance of the control over previous 60 minute time window, using the following steps:

(a) Calculate proportion of time in eupoxic, hypoxic and hyperoxic ranges:
  $t_{severe\ hypoxia}$: SpO$_2$<80%.
  $t_{hypoxia}$: 80%<=SpO$_2$<=84%.
  $t_{eupoxia}$: SpO$_2$ in target range, or above with FiO$_2$=21%.
  $t_{hyperoxia}$: 97%<=SpO$_2$<99% when receiving oxygen.
  $t_{severe\ hyperoxia}$: SpO$_2$>=99% when receiving oxygen
  (i.e., quantify the total time of hypoxia, severe hypoxia, hyperoxia, severe hyperoxia and eupoxia).

(b) Calculate weighted performance coefficient:

$$C_{performance} = (t_{severe\ hyperoxia} + t_{hyperoxia})(t_{hypoxia} + t_{severe\ hypoxia})$$

(i.e., the ratio of time in hyperoxia including severe hyperoxia to time in hypoxia including severe hypoxia, indicating an underpowered and overpowered K$_p$).

(c) Calculate new Kp:
  If $C_{performance}$ <=0.7, K$_p$=K$_p$*1.1.
  If 0.7<$C_{performance}$ <=0.85, K$_p$=K$_p$*1.05.
  If 1.15<=$C_{performance}$ <1.3, K$_p$=K$_p$*0.95.
  If $C_{performance}$ >=1.3, K$_p$=K$_p$*0.9.
  (i.e., alter the value of K$_p$ based on the ratio of time)

(d) Calculate eupoxia time:
  eupoxia time=($t_{eupoxia}$×100)/$t_{total}$.
  (i.e., proportion of time in which SpO$_2$ was in an eupoxic range)
  If eupoxia time <target range adherence goal,
  alarm: "target range adherence"=true
  (i.e., an alarm is triggered if the automatic control was below the minimum requirement).

Further, the method for automatically controlling inspired oxygen delivery may further include:

(a) generating an rFiO$_2$ evaluation result based on the input SpO$_2$ values and the respective output FiO$_2$ values over an rFiO$_2$ evaluation time period; and (b) modifying the rFiO$_2$ value based on the rFiO$_2$ evaluation result.

The rFiO$_2$ value may have an initial value and may be modified repeatedly over time.

In some embodiments, the analysis may be performed on a regular basis. For example, the analysis may be performed once every 30 minutes, which may be referred to the evaluation time frequency. The analysis may also be performed once after each of a certain interval, which may be any suitable time between 30 minutes and 2 hours. At the evaluation time frequency, an analysis of the relationship between set FiO$_2$ and SpO$_2$ in a shifting time window (an "evaluation time period") may be undertaken, with the assumption that a fixed V/Q ratio, along with a variable shunt, caused the oxygenation disturbances. The time window may be 60 minutes, or any suitable time period (any selected period from 30 minutes to 2 hours). A value for V/Q ratio may then be derived, e.g., using known ways and formulae for calculating V/Q ratio, and from it the rFiO$_2$ value may be modified for overcoming its effect on oxygenation. This may become the new value for rFiO$_2$, which may be coerced to within ±10% of the previous value. Rapid changes in rFiO$_2$ may thus be avoided.

Figure 5:
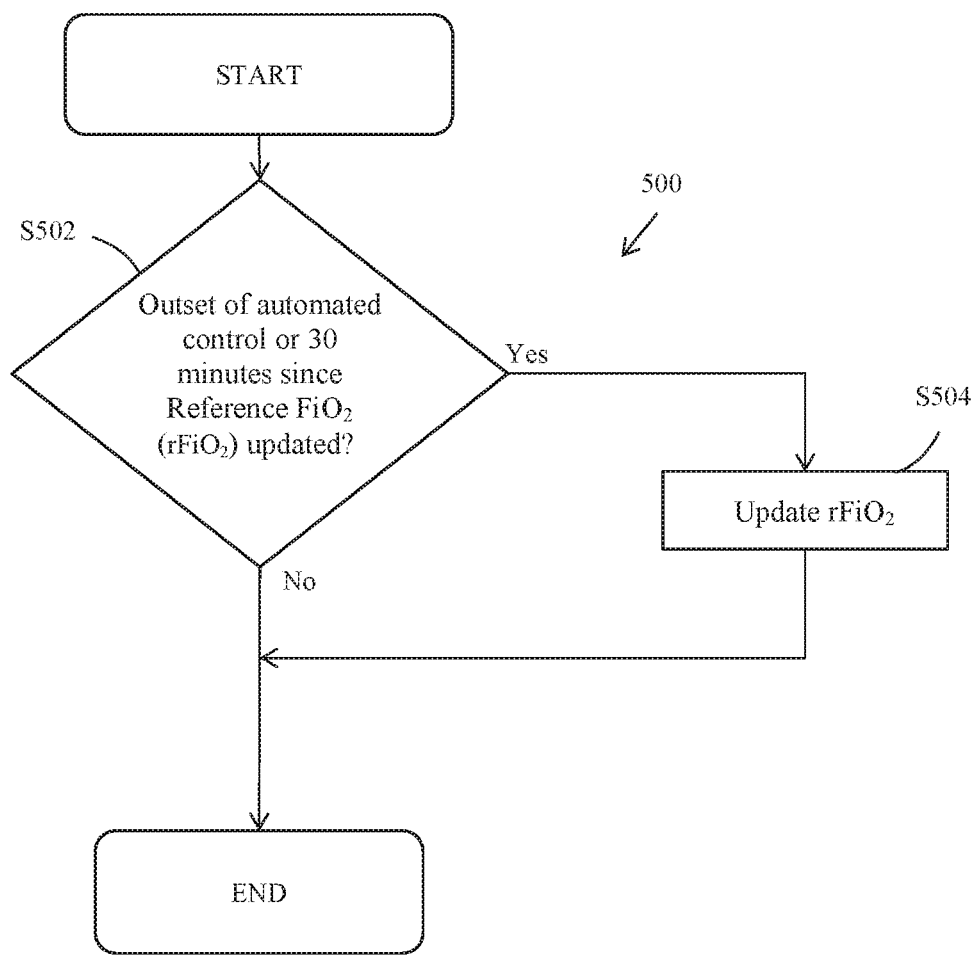
FIG. 5 is a flow chart depicting a process of modifying the value of $rFiO_2$.

FIG. 5 illustrates a process 500 performed by the controller 11 of modifying the value of rFiO$_2$.

As shown in FIG. 5, in S502, the process 500 determines whether it is outset of automated control or 30 minutes have elapsed since last time reference FiO$_2$ (rFiO$_2$) was updated.

If the result of determination is no, the process 500 ends. If it is determined that it is outset of automated control or 30 minutes have elapsed, the process 500 moves to S504 to update the value of rFiO$_2$, using the following steps:

(a) Sliding-window analysis
  Perform 60 minute sliding-window analysis of FiO$_2$ and SpO$_2$ to obtain V/Q ratio, and obtain rFiO$_2$ from V/Q ratio.

(b) Coerce rFiO$_2$ to within ±10% of the previous value

If $(rFiO_2 - \text{previous } rFiO_2)/(\text{previous } rFiO_2) > 0.1$, $rFiO_2$=previous $rFiO_2$+sign($rFiO_2$−previous $rFiO_2$)*0.1*previous $rFiO_2$ (i.e., determine the new value of rFiO$_2$, coerced to within ±10% of the previous value; rapid changes in rFiO$_2$ may thus be avoided).

(c) At the outset of automated control, use the current value for FiO$_2$ or a value input by the user as the starting value for rFiO$_2$.

In addition, the method for automatically controlling inspired oxygen delivery may further include:

(a) generating a SpO$_2$ validation result based on a current input SpO$_2$ value by classifying a current input SpO$_2$ value into one of multiple validity levels in a hierarchical validation procedure; and (b) determining the output FiO$_2$ value based on the SpO$_2$ validation result.

The following hierarchical validation levels may be adopted:

(a) "Level I", corresponding to the SpO$_2$ input "missing", if the SpO$_2$ input meets a first condition;

(b) "Level II", corresponding to the SpO$_2$ input being "suspect", if the SpO$_2$ input meets a second condition; and (c) "Level III", correspond to the SpO$_2$ input being "invalid", if the SpO$_2$ input meets a third condition.

Further, in some embodiments, the method may further include:

receiving at least one of:
- a signal representing a heart rate derived from a SpO$_2$ plethysmographic waveform;
- a signal representing a heart rate derived from electrocardiographic monitoring; and
- a signal representing a perfusion index;

wherein the validity of the current input SpO$_2$ value is determined based on at least one of:
- the received heart rate derived from a SpO$_2$ plethysmographic waveform;
- the received heart rate derived from electrocardiographic monitoring; and
- the received perfusion index.

For validation of the SpO$_2$ signal, some or all of the following ancillary inputs may be sourced as digital signals:

(a) a heart rate derived from the SpO$_2$ plethysmographic waveform (HR$_{pleth}$);
(b) a heart rate derived from electrocardiographic monitoring (HR$_{ecg}$); and
(c) perfusion index, this being a metric of oximetry waveform pulsatility, with low values potentially associated with spurious SpO$_2$ values.

At the outset of automated control, and then each 24 hours (the "perfusion check period"), a perfusion index value representing optimum perfusion may recorded at a time when the plethysmographic waveform is stable and the signal is strong. The perfusion check period may be any suitable time period, including any selected time period from 6 hours to 2 days.

Figure 6:
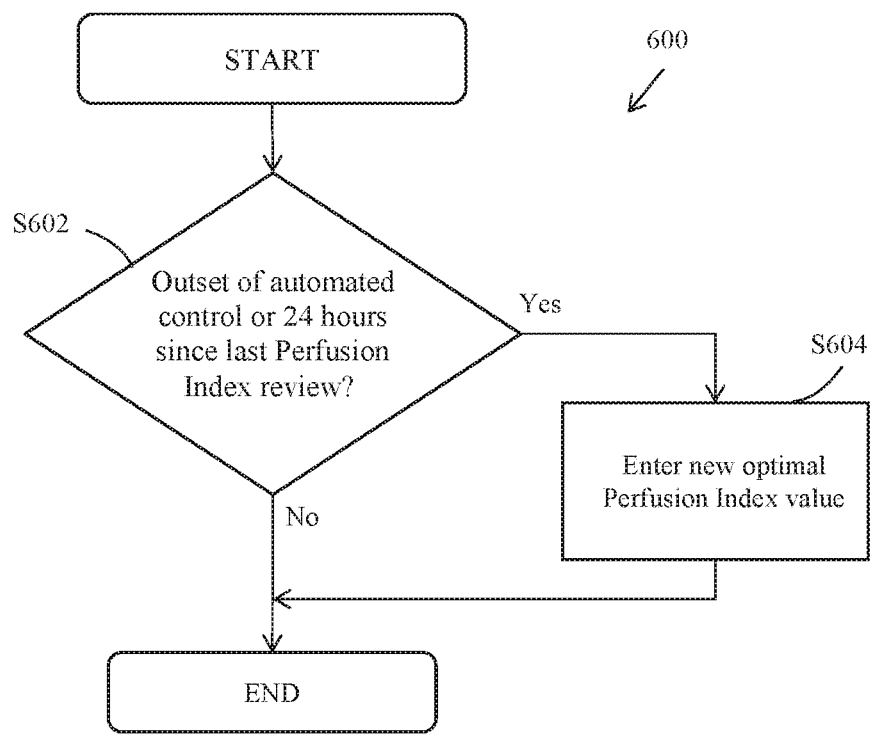
FIG. 6 is a flow chart depicting a process of determining the perfusion index value.

FIG. 6 illustrates a process 600 performed by the controller 11 of determining the perfusion index value.

As shown in FIG. 6, in S602, the process 600 determines whether it is outset of automated control or 24 hours have elapsed since last perfusion index review.

If the result of determination is no, the process 600 ends. If it is determined that it is outset of automated control or 24 hours have elapsed, the process 600 moves to S604 to enter a new optimal perfusion index value, e.g., being the 95th centile over the last 24 hours.

The plethysmographic waveform, which can be recorded over the preceding 10 seconds (or any suitable time period, including any selected time period from 5 seconds to 20 seconds) may also be input as an analogue signal that was digitised with the aid of an analogue-digital converter. Digital and analogue signals may be acquired using a data acquisition device.

Waveform analysis validates the SpO$_2$ by analysing the plethysmographic signal from the pulse oximeter to confirm it is conformant to the properties expected from a valid plethysmographic signal. Assessment methods include, either individually or in combination, analysis of statistical properties of the signal (such as mean and variance), classic signal processing techniques (such as autocorrelation), logical algorithms (including fuzzy logic) and pattern recognition techniques (including neural networks).

For example, one exemplary process for carrying out the SpO$_2$ plethysmographic waveform analysis includes the following steps:

(a) periodically obtaining a valid "representative" plethysmographic tracing from the individual patient;
(b) normalising the current input SpO$_2$ plethysmographic signal in two axes, so that so that both the periodicity and the peak and trough amplitudes correspond with the 'representative' plethysmographic tracing;
(c) comparing the two signals by multiple linear regression, with the mean-squared error giving an indication of the departure of the current signal from the 'representative' SpO$_2$ plethysmographic waveform.

Alternatively, the two signals may be compared by other methods, for example pattern recognition, such as linear discriminant analysis or artificial neural networks. Using these methods, a pre-recorded database of recordings of plethysmographic waveform signals with SpO$_2$ classified as valid or invalid may be used for training and validation of the pattern recognition such that it may be used to classify the monitored SpO$_2$ signal as valid or invalid.

With these additional inputs, the following hierarchical validation procedure may be adopted:

(a) Level I: if the SpO$_2$ value is zero or non-numeric;
(b) Level II: if, after normalisation in both axes, the waveform does not conform with a generic plethysmographic waveform; and
(c) Level III: if:
  i. perfusion index is <30% (or any other suitable value, e.g., any value between 10% and 50%) of the optimum value and the waveform is "suspect", or
  ii. absolute value of HR$_{ecg}$–HR$_{pleth}$>30 bpm (or any other suitable value, e.g., any value between 20 bpm and 50 bpm) and the waveform is "suspect", or
  iii. there is a precipitous fall in SpO$_2$ (e.g., >15% in 5 seconds, or any other suitable value representing a sudden and deep drop in SpO$_2$, where the drop needs to last for a certain time period, e.g., 5 seconds, since sometimes a sudden drop in SpO$_2$ may be a spurious reading), along with any of: "suspect" waveform, heart rate discrepancy or perfusion index discrepancy (suggesting spurious hypoxia).

Figure 7:
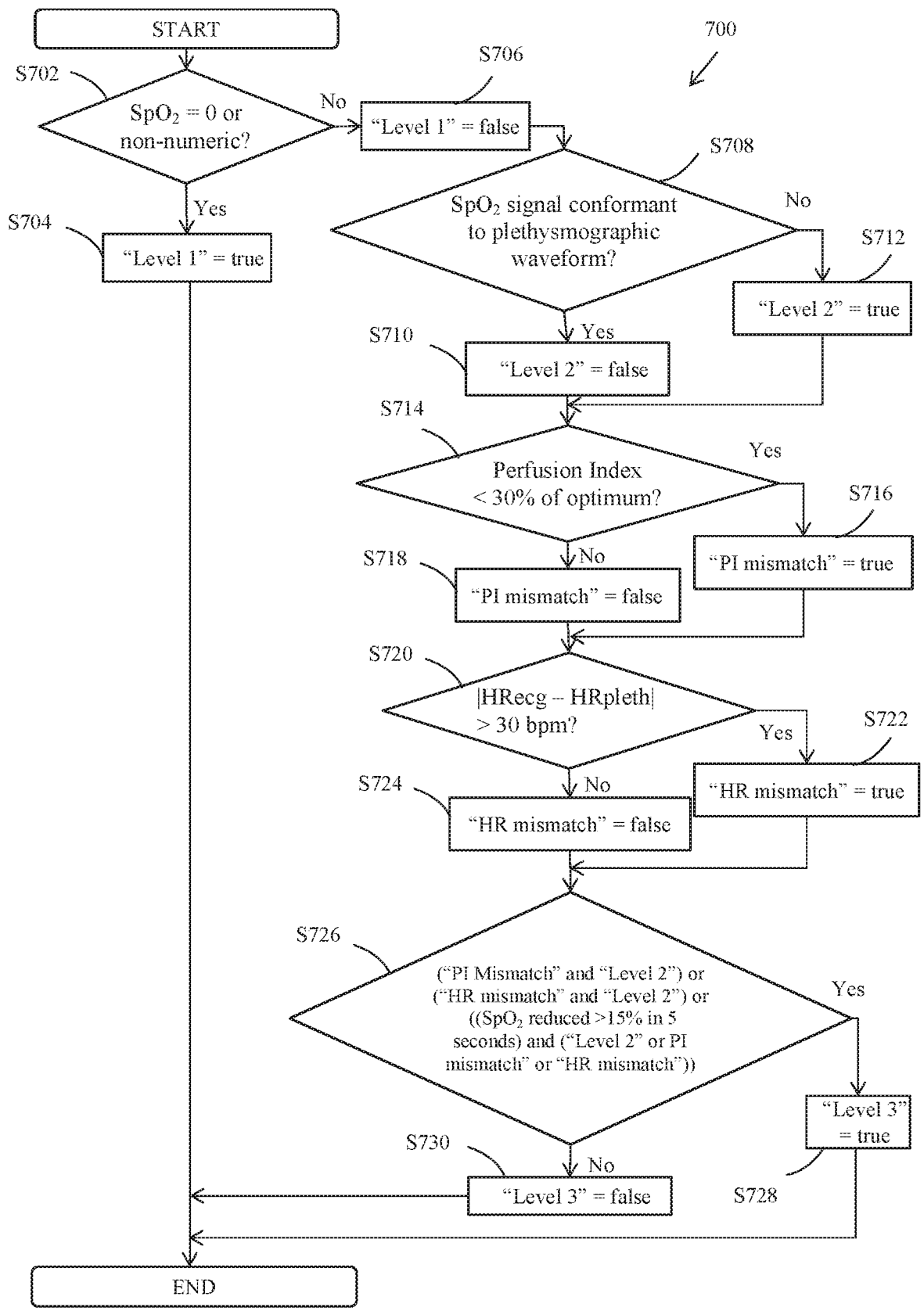
FIG. 7 is a flow chart depicting a process of the hierarchical $SpO_2$ validation procedure.

FIG. 7 depicts an example of the hierarchical validation process (700) performed by the controller 11.

As shown in FIG. 7, first, it is determined in S702 whether the input SpO$_2$ value is zero or non-numeric. If yes, a flag "Level 1" is set as true (S704) and the process 700 ends.

If the input SpO$_2$ value is not zero or non-numeric, the flag "Level 1" is set as false (S706) and a further determination is performed in S708 to test the input SpO$_2$ signal's conformant to plethysmographic waveform. If it is determined that, after normalisation in both axes, the waveform of the input SpO$_2$ signal does not conform with a generic plethysmographic waveform, a flag "Level 2" is set as true (S712), i.e., the SpO$_2$ input is "suspect". If the waveform of the input SpO$_2$ signal conforms to a generic plethysmographic waveform, the flag "Level 2" is set as false.

Next, the logic moves to S714 to determine whether the perfusion index is <30% of the optimum, and sets a flag "PI mismatch" as true if the perfusion index is <30% of the optimum (S716), or sets the flag "PI mismatch" as false if not (S718).

Next, a test is performed in S724 to determine whether the absolute value of HR$_{ecg}$–HR$_{pleth}$ >30 bpm in S720. If yes, a flag "HR mismatch" is set as true (S722); and if not, the flag "HR mismatch" is set as false (S724);

Further, it is determined in S726 that whether a "Level III" condition is satisfied, i.e., whether the SpO$_2$ input is "invalid", e.g., by using the following logic:

("PI Mismatch" and "Level 2") or ("HR mismatch" and "Level 2") or
((SpO$_2$ reduced >15% in 5 seconds) and ("Level 2" or PI mismatch" or "HR mismatch"))

If the result is positive, a "Level III" flag is set as true (S728), i.e., the SpO$_2$ input is "invalid"; if not, the "Level III" flag is set as false (S730).

In some embodiments, when the input $SpO_2$ value is determined as being invalid (e.g., in the event of missing or invalid signal), the $FiO_2$ may be set to hold the output $FiO_2$ value at the current value, i.e., the previously recorded $FiO_2$ value. In the event of prolonged missing or invalid signal, beyond the triggering of alarms described hereinafter, the output $FiO_2$ value may be trended towards the $rFiO_2$.

Figure 8:
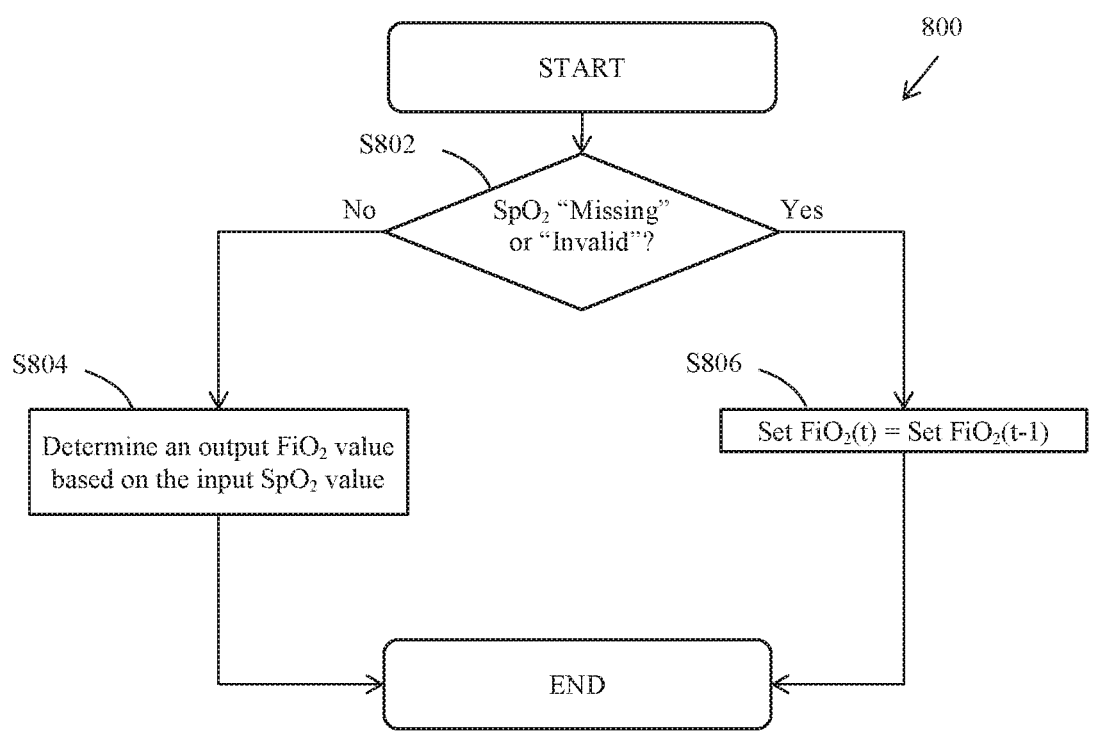
FIG. 8 is a flow chart depicting a process of determining the output $FiO_2$ value based on the validity of $SpO_2$.

FIG. 8 illustrates a process 800 performed by the controller 11 for determining the output $FiO_2$ value based on the validity of $SpO_2$.

As shown in FIG. 8, a test is carried out in S802 to decide whether the input $SpO_2$ value is "Missing" or "Invalid". If it is determined that the input $SpO_2$ value is "Missing" or "Invalid", the output $FiO_2$ value is set the same as the previous output $FiO_2$ value in S806. If in S802 it is held that the input $SpO_2$ value is not "Missing" or "Invalid", the logic moves to S804, where an output $FiO_2$ value is determined based on the input $SpO_2$ value, e.g., using the following steps:

(a) Calculate $\Delta FiO_2$: $\Delta FiO_2 = P(t) + I(t) + D(t)$.
(b) Calculate output $FiO_2$ value: $FiO_2 = \Delta FiO_2 + rFiO_2$
(c) If apnoea >15 sec, alter output $FiO_2$ value up by 5% for 30 sec beyond apnoea cessation.
(d) Round "output $FiO_2$ value" to ±0.5%.
(e) If $FiO_2$<21%, output $FiO_2$ value=21%.
If $FiO_2$>100%, output $FiO_2$ value=100%.

In some embodiments, an alarm (e.g., an audible and/or a visible alarm) may be activated when the $SpO_2$ is determined as having been invalid for a certain time period (e.g., 30 seconds, or any other suitable time period which can prevent continuously missing out a signal from a baby who has been having a low $SpO_2$). For example, the alarm may be an audible alarm, and the volume of the alarm may increase every few minutes (e.g., 2 minutes) when the alarm is being activated, with an error message to check the oximeter probe and connections.

In some embodiments, the alarm may be terminated and determination of the output $FiO_2$ value based on the immediate control value, the accumulation control value, the predictive control value and the reference inspired oxygen concentration may resume as soon as a valid $SpO_2$ is detected.

In addition, the method for automatically controlling inspired oxygen delivery may further include:
(a) receiving a signal representing a respiratory rate;
(b) wherein the immediate control value is generated further based on the respiratory rate.

In some embodiments, respiratory rate may be recorded with an abdominal capsule linked to a respiration monitor, from which with every detected spontaneous breath a digital pulse may be routed to the automatic controller via an analogue-digital converter.

Episodes of respiratory pause (e.g., 5 to 15 seconds of breathing cessation, or a breathing cessation for any suitable time period sufficient for predicting a likely hypoxic event) and apnoea (e.g., longer than 15 seconds or longer than any suitable time period sufficient for predicting a likely hypoxic event) may be identified.

The value of $K_p$ may be modified based on this additional input.

For example, a respiratory pause may result in a doubling of $K_p$ for a certain time period (e.g., 30 seconds, or any suitable time period) beyond the cessation of breathing. Through this adjustment, the automatic controller is more sensitive in its response to a hypoxic event if one occurs. If the respiratory pause continues into frank apnoea, the $FiO_2$ may also be transiently increased 2 to 8% in proportion to the underlying $K_p$ value.

In addition, the method for automatically controlling inspired oxygen delivery may further include:
(a) receiving a signal representing a circuit pressure;
(b) wherein the immediate control value is generated further based on the circuit pressure.

For infants on continuous positive airway pressure (CPAP) respiratory support, the pressure in the inspiratory limb of the CPAP circuit may be transduced, and input as a digital signal.

For example, reduction in circuit pressure to levels below a certain proportion (including any selected value between 20% and 50%) of the plateau value may lead to doubling of $K_p$, and, after 30 seconds, triggering of an alarm representing a circuit pressure reduction. Complete loss of circuit pressure (<1 cm $H_2O$, i.e., when there is essentially no pressure being delivered) may trigger a higher level alarm representing circuit pressure loss.

In some embodiments, the method may further include:
receiving an manual override input;
determining the output $FiO_2$ value based on the manual override input instead of the control values.

Further, the controlling apparatus 10 may have an automatic control mode and a manual control mode, and the automatic control mode can be switched to the manual control mode under certain user inputs (i.e., the manual override inputs), and subsequently reverted back to automatic mode if desired.

For example, a user (e.g., bedside staff) may switch the controlling apparatus 10 into a manual control mode, such that the controller 11 no longer produced changes in the output $FiO_2$ value, and oxygenation is entirely under manual control.

Manual control mode may be selected through a manual override input in the user interface displayed on the user-interface display 14. It may be either as a temporary halt (e.g., 30 seconds duration) in the function of the controller producing changes in $FiO_2$, or as continuous manual operation until deselected.

The manual control mode may be also be selected by rotating the $FiO_2$ selection dial on the automated air-oxygen blender, i.e., providing a manual override input to trigger a halt to automated control (e.g., a halt of 30 second or any selected suitable time period).

In the first iteration after the halt, i.e., returning from manual control mode, the integrand may be adjusted such that the output $FiO_2$ value is set equal to the current (i.e., user-selected) value of servo $FiO_2$, with automated control resumed thereafter.

Figure 9:
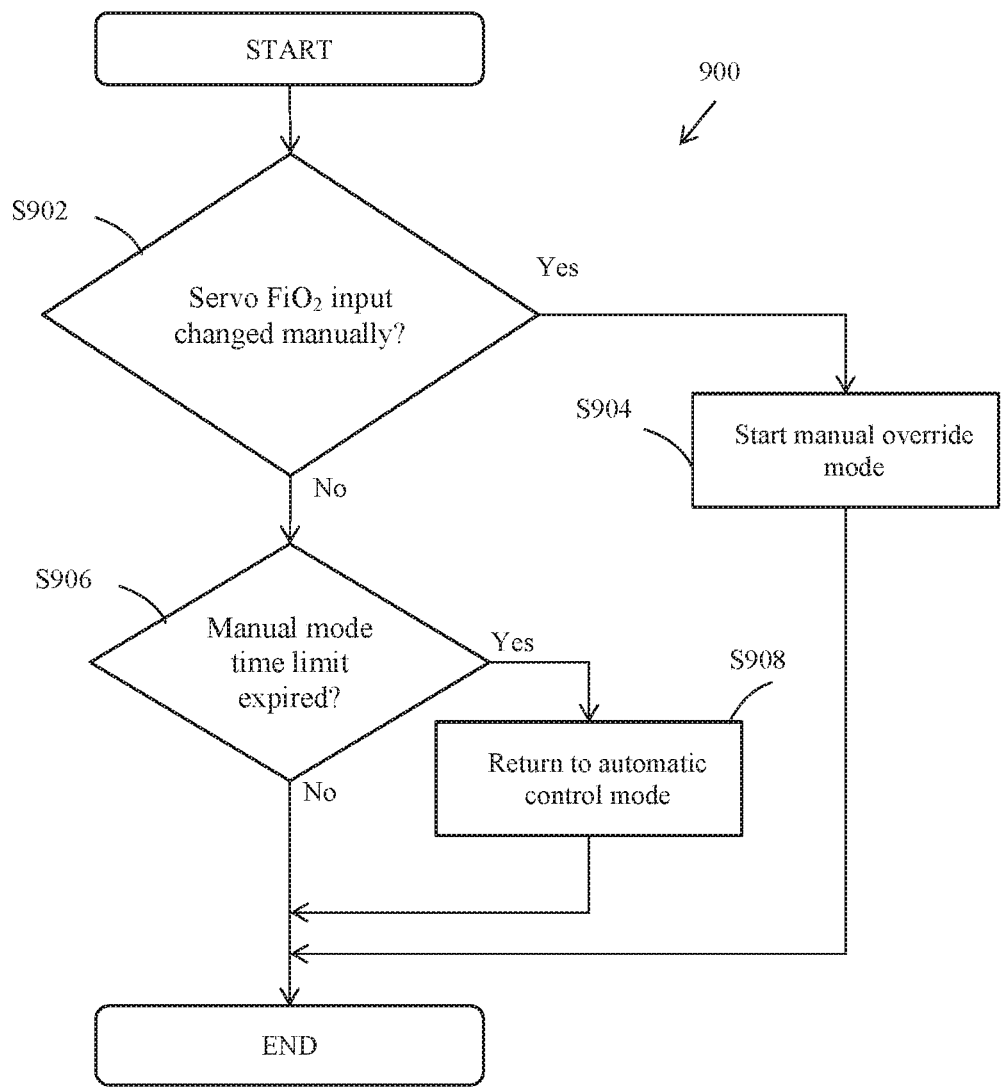
FIG. 9 is a flow chart depicting a process of switching between the manual mode and the automatic control mode.

FIG. 9 illustrates a process 900 performed by the controller 11 for switching between the manual mode and the automatic control mode.

As shown in FIG. 9, first, a test is carried out in S902 to determine whether the servo $FiO_2$ input has been changed manually, i.e., a manual override input received. If yes, a manual override mode is started in S904. If the servo $FiO_2$ input has not been changed manually, the logic moves to S906 to determine whether the manual mode time limited has expired. If the manual mode time limited has expired, the controlling apparatus 10 is then set to return to automatic control mode in S908. If the manual mode time limited has not expired, the process 900 ends.

Further, one or more alarms may be triggered under certain condition during the automatic control.

For example, alarms (e.g., audible and/or visible alarms) may be included in the controlling apparatus 10, alerting bedside staff to rapidly rising $FiO_2$, achievement of maximum $\Delta FiO_2$, missing or invalid $SpO_2$ signal for >30 sec and >2 min, prolonged apnoea or circuit pressure loss, and system malfunction. These alarms may be added to, integrated with, or supplant, the alarms set within standard bedside monitors in the NICU.

Figure 10:
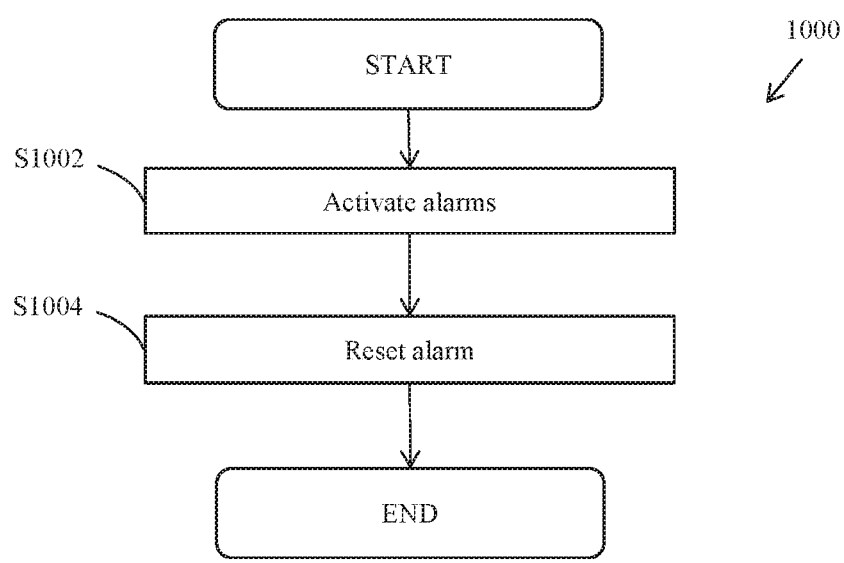
FIG. 10 is a flow chart depicting a process of controlling and resetting alarms.

FIG. 10 illustrates a process 1000 performed by the controller 11 of controlling alarms based on by monitoring various signals described hereinbefore.

As shown in FIG. 10, in S1002 a process of activating alarms is performed, using the following steps:
- (a) If alarm: "missing signal"=true, activate missing signal alarm.
- (b) If alarm: "hypoxia"=true, activate hypoxia alarm.
- (c) If alarm: "circuit pressure reduction"=true, activate circuit pressure reduction alarm.
- (d) If alarm: "circuit pressure loss"=true, activate circuit pressure loss alarm.
- (e) If alarm: "servo $FiO_2$ mismatch"=true, activate servo $FiO_2$ mismatch alarm.
- (f) If alarm: "servo $FiO_2$ error"=true, activate servo $FiO_2$ error alarm.
- (g) If alarm: "measured $FiO_2$ mismatch"=true, activate measured $FiO_2$ mismatch alarm.
- (h) If alarm: "measured $FiO_2$ error"=true, activate measured $FiO_2$ error alarm.
- (i) If alarm: "target range adherence"=true, activate target range adherence alarm.

Next, the process 1000 moves to S1004, where alarms are reset using the following steps:
- (a) If missing signal alarm reset, alarm ("missing signal")=false.
- (b) If hypoxia alarm reset, alarm ("hypoxia")=false.
- (c) If circuit pressure reduction alarm reset, alarm ("circuit pressure reduction")=false.
- (d) If circuit pressure loss alarm reset, alarm ("circuit pressure loss")=false.
- (e) If servo $FiO_2$ alarm reset, alarm ("servo $FiO_2$ mismatch")=false.
- (f) If servo $FiO_2$ alarm high reset, alarm ("servo $FiO_2$ error")=false.
- (g) If measured $FiO_2$ alarm reset, alarm ("measured $FiO_2$ mismatch")=false.
- (h) If measured $FiO_2$ high alarm reset, alarm ("measured $FiO_2$ error")=false.
- (i) If target range adherence alarm reset, alarm ("target range adherence")=false.

After finishing S1004, the process 1000 ends.

Further, as described hereinbefore, the controlling apparatus 10 may further include a user-interface display 14, which displays a user interface showing various information to a user (e.g., a bedside caregiver) and receiving instructions inputted by the user based on the user-interface. The received user inputs are then transmitted to the controller 11.

Figure 11:
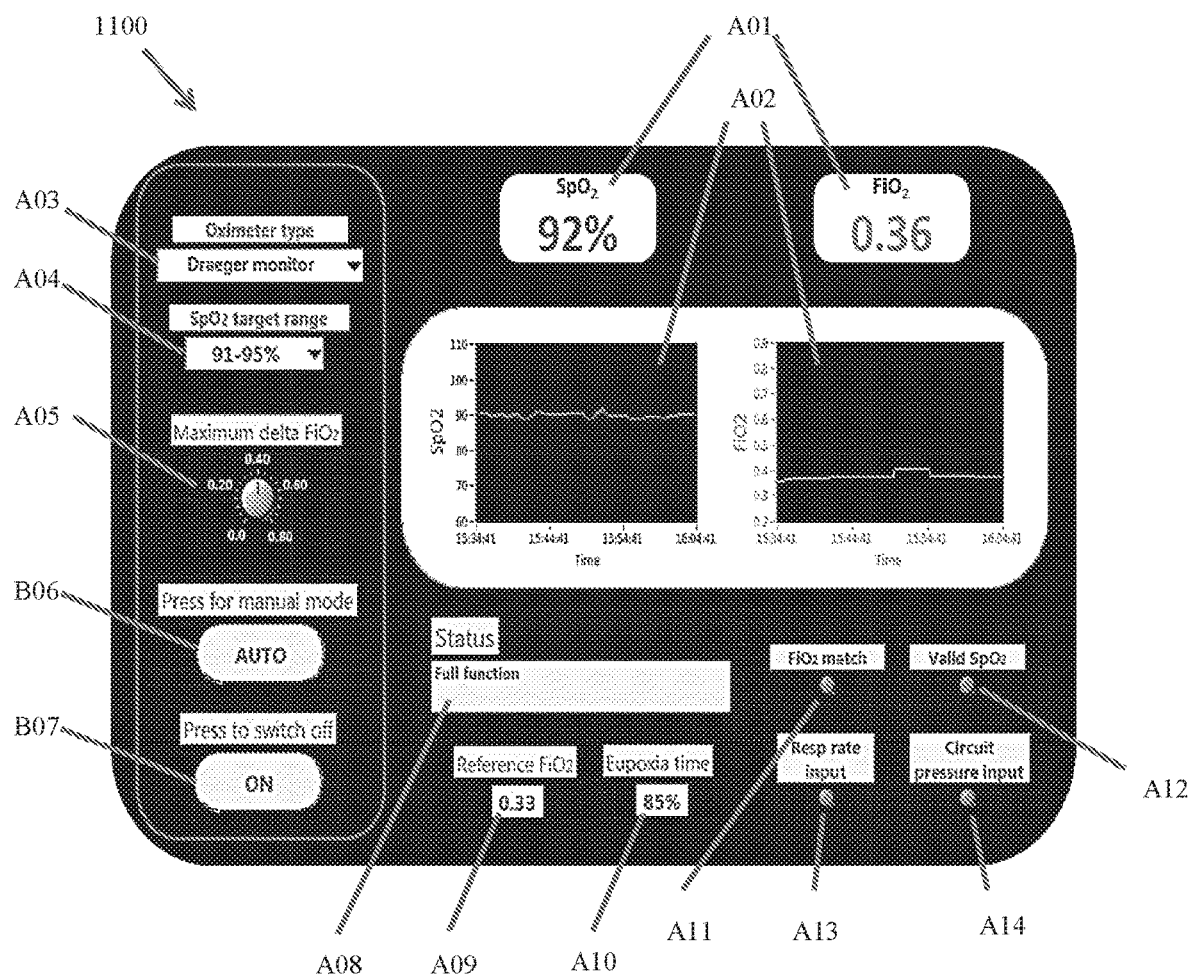
FIG. 11 is a diagram of a user interface of the oxygen delivery system apparatus.

One example of a user interface 200 displayed on the user-interface display 14 is illustrated in FIG. 11. The user interface 200 may include:
- (a) a numerical $SpO_2/FiO_2$ display area A01, displaying the latest input $SpO_2$ value and the latest output $FiO_2$ value;
- (b) a graphical $SpO_2/FiO_2$ display area A02, graphically displaying the trend of input $SpO_2$ values and the output $FiO_2$ values;
- (c) an oximeter type choosing area A03, for a user to choose the type of oximeter used for generating the $SpO_2$ signal;
- (d) a $SpO_2$ target range setting area A04, for displaying and allowing a user to alter the target $SpO_2$ range in real-time;
- (e) a maximum $\Delta FiO_2$ setting area A05, for indicating and allowing a user to alter a limitation for the value of $\Delta FiO_2$ in real-time;
- (f) a manual control mode button B06, by pressing which the controlling apparatus 10 can be switched between an automatic control mode and a manual control mode;
- (g) an on/off button B07, by pressing which the controlling apparatus 10 can be turned on or turned off;
- (h) a status display area A08, displaying the working status of the controlling apparatus 10, which may include displaying visible alarm information under certain conditions;
- (i) a reference $FiO_2$ display area A09, displaying the most recent values for $rFiO_2$;
- (j) an eupoxia time display area A10, displaying the proportion of time in eupoxia;
- (k) $FiO_2$ feedback indicating area A11, indicating whether the servo $FiO_2$ or measured $FiO_2$ matches the output $FiO_2$ value, e.g., by a light indicator;
- (l) valid $SpO_2$ indicating area A12, indicating whether the input $SpO_2$ value is valid, e.g., by a light indicator; and
- (m) additional inputs indicating areas A13 and A14, indicating respectively whether signals representing a respiratory rate and a respiratory circuit pressure have been inputted into the controlling apparatus 10, e.g., by light indicators.

Figure 12:
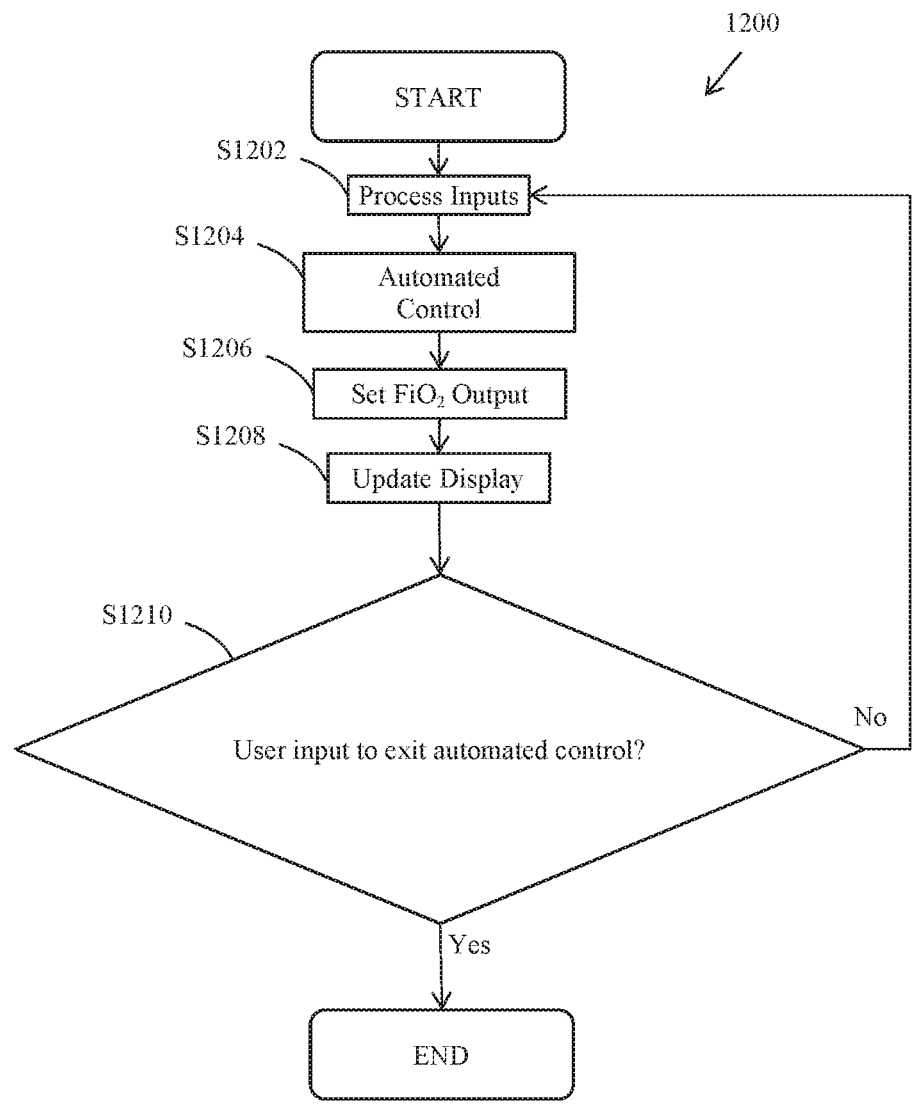
FIG. 12 is a flow chart depicting a general control process of the method for automatically controlling inspired oxygen delivery.

A general control process of the method for automatically controlling inspired oxygen delivery performed by the controller 11 according to some embodiments is depicted by the flow chart in FIG. 12.

As shown in FIG. 12, when the control process has started, inputs to the controlling apparatus 10 are processed in S1202.

Figure 13:
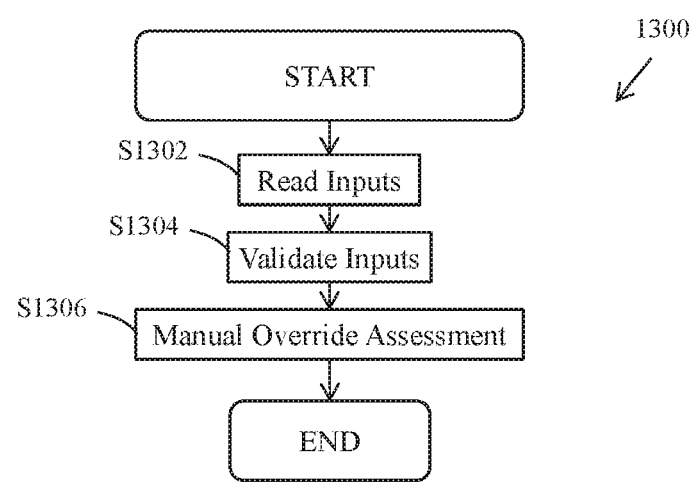
FIG. 13 is a flow chart depicting a process of processing inputs.

FIG. 13 depicts exemplary steps (1300) of processing inputs in S1202: the inputs are read from the input unit (S1302), and then validated (S1304). After the validation of the inputs, a manual override assessment is performed (S1306).

Figure 14:
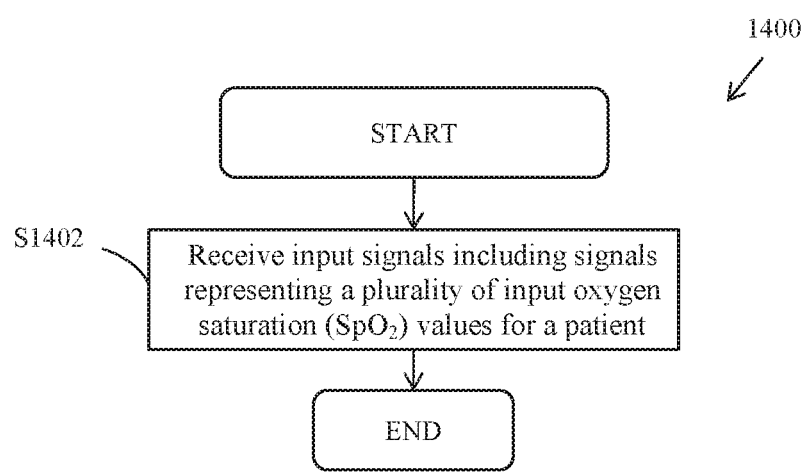
FIG. 14 is a flow chart depicting a process of reading inputs.

Exemplary steps of reading inputs in S1302 are as illustrated in FIG. 14. As shown in FIG. 14, in S1402, input signals including signals representing a plurality of input oxygen saturation ($SpO_2$) values for a patient are received. The input signals may include: $SpO_2$, $HR_{pleth}$, Perfusion Index, Pleth waveform, $HR_{ecg}$, Respiration Rate, CPAP Circuit Pressure, Servo $FiO_2$, Measured $FiO_2$, $\Delta FiO_2$max, $SpO_2$ target, Target range adherence goal.

Figure 15:
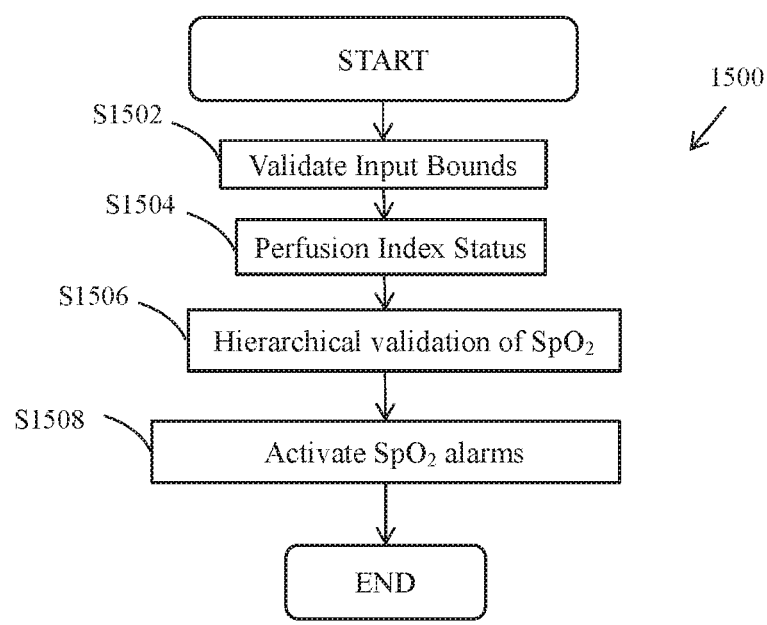
FIG. 15 is a flow chart depicting a process of validating inputs.

Exemplary steps of the validation of the inputs in S1304 are as illustrated in FIG. 15. First, validation of input bounds is performed in S1502, after which the perfusion index status is updated in S1504. A hierarchical validation of $SpO_2$ is then performed in S1506. Further, alarms may be triggered based on the result of the hierarchical validation of $SpO_2$ and based on whether servo $FiO_2$ or measured $FiO_2$ deviating from set $FiO_2$ beyond tolerance limits (1 and 2%, respectively) in S1508.

Activating alarms in S1508 may adopt the following steps:
- (a) If $SpO_2$ signal is Level 1 or Level 3 for >30 sec, alarm: "missing signal"=true.
  If $SpO_2$ signal is Level 1 or Level 3 for >2 min, increase volume of alarm: "missing signal"

error message to check the oximeter probe and connections (b) If |(set $FiO_2$-servo $FiO_2$)/(set $FiO_2$)|>1%,
alarm: "servo $FiO_2$ mismatch"=true.
If |(set $FiO_2$-servo $FiO_2$)/(set $FiO_2$)|>5%,
alarm: "servo $FiO_2$ error"=true, and ManualMode=true;

(c) If |(set $FiO_2$-measured $FiO_2$)/(set $FiO_2$)|>2%,
alarm: "measured $FiO_2$ mismatch"=true.
If |(set $FiO_2$-measured $FiO_2$)/(set $FiO_2$)|>10%,
alarm: "measured $FiO_2$ error"=true, and ManualMode=true.

Figure 16:
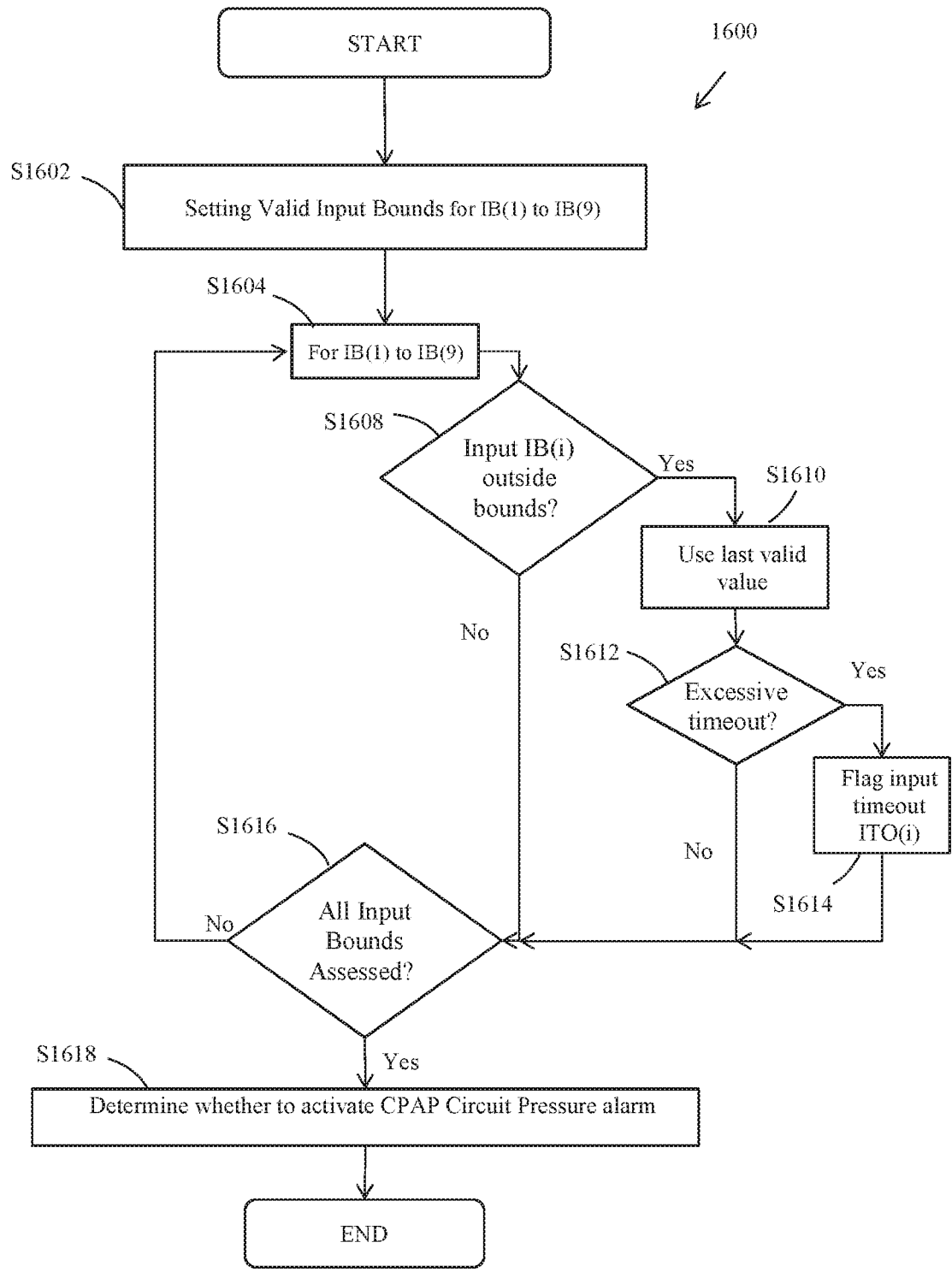
FIG. 16 is a flow chart depicting a process of validation of input bounds.

Further, FIG. 16 illustrates exemplary steps of validation of input bounds in S1502.

As shown in FIG. 16, first, valid input bounds are set in S1602. For example, valid input bounds for IB(1)-IB(9) may be set as the following:

| | | |
|---|---|---|
| IB(1) | $SpO_2$: | 0 <= $SpO_2$ <= 100% |
| IB(2) | $HR_{pleth}$: | 0 <= $HR_{pleth}$ <= 300 bpm |
| IB(3) | Perfusion Index: | 0 <= Perfusion Index <= 10 |
| IB(4) | Pleth waveform: | 0 <= Pleth waveform <= 5 V |
| IB(5) | $HR_{ecg}$: | 0 <= $HR_{ecg}$ <= 300 bpm |
| IB(6) | Respiration Rate: | 0 <= Respiration Rate <= 150/min |
| IB(7) | CPAP Circuit Pressure: | 0 <= CPAP Circuit Pressure <= 20 cm $H_2O$ |
| IB(8) | Servo $FiO_2$: | 21% <= Servo $FiO_2$ <= 100% |
| IB(9) | Measured $FiO_2$: | 21% <= Measured $FiO_2$ <= 100% |

Next, through the loop in S1604, S1608 and S1616, a determination is made to decide whether the input value of each IB(i) is outside the valid input bound. If not, the loop proceeds to determine the next IB(i). If yes, the logic moves to S1610, where last valid value for IB(i) is used instead of the current IB(i). After S1610, a test is carried out to determine whether an excessive timeout has occurred (S1612). If yes, an input timeout flag ITO(i) is set (S1614), and the logic proceed to S1616 to process the next IB(i) or finish the input bounds assessment.

When all IB(i) have been validated, the logic moves to S1618 to determine whether a alarm should be activated based on the current value of CPAP circuit pressure, e.g., using the following steps:

a. Valid Circuit Pressure is in-range:
if CPAP Circuit Pressure <50% of the plateau value,
CPAP Circuit Pressure=low
(i.e., if the circuit pressure is below 50% of the plateau value, determine that the circuit pressure as low);
if CPAP Circuit Pressure <1 cm $H_2O$,
CPAP Circuit Pressure=loss.
(i.e., if the circuit pressure is below 1 cm $H_2O$ of the plateau value, determine that the circuit pressure is completely lost);

b. Activate CPAP Circuit Pressure alarms:
if CPAP Circuit Pressure low for >30 seconds,
activate alarm: "circuit pressure reduction"
(i.e., the circuit pressure has been below 50% for more than 30 seconds, trigger an alarm).

Updating the perfusion index status in S1504 may adopt the process illustrated in FIG. 6 as described before.

The hierarchical validation of $SpO_2$ in S1506 may adopt the process illustrated in FIG. 7 as described before.

Manual override assessment in S1306 may adopt the process illustrated in FIG. 9 as described before.

After processing inputs in S1202, an automated control is performed (S1204), determining the $FiO_2$ values based on the input $SpO_2$ values.

Figure 17:
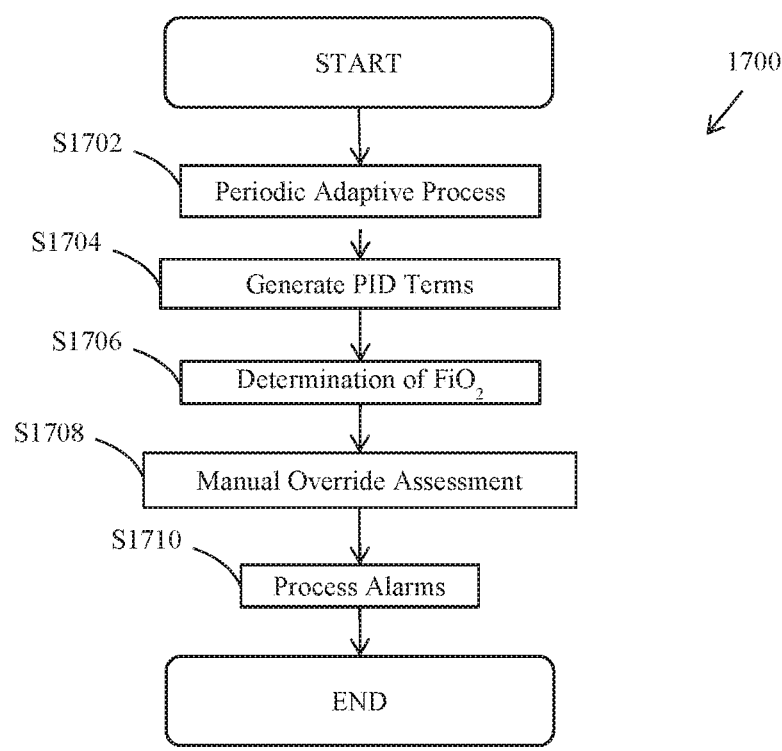
FIG. 17 is a flow chart depicting a process of the automated control.

FIG. 17 depicts the exemplary steps of the automated control in S1204. As shown in FIG. 17, once the automated control starts, a periodic adaptive process is first performed (S1702).

Figure 18:
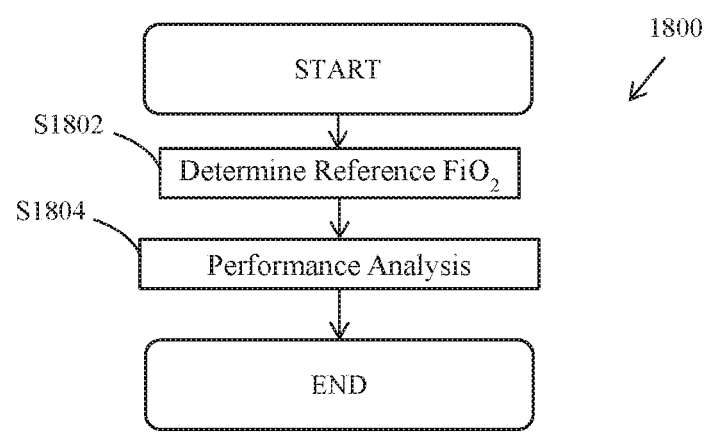
FIG. 18 is a flow chart depicting a periodic adaptive process.

Exemplary steps of the periodic adaptive process in S1702 are depicted by the flow chart in FIG. 18. As illustrated in FIG. 18, the periodic adaptive process may include updating the reference $FiO_2$ (S1802) and performance analysis (S1804), which may adopt the exemplary process as illustrated in FIG. 5 and FIG. 4 (as described hereinbefore) respectively.

After the periodic adaptive process in S1702, the PID terms are generated in S1704. The exemplary process as illustrated in FIG. 3 as described before may be adopted by S1704.

In S1706, an output $FiO_2$ value is determined based on the PID terms, a $rFiO_2$ value and the validity of the input $SpO_2$ value. The exemplary process as illustrated in FIG. 8 as described before may be adopted for determining the output $FiO_2$ value in S1706.

In S1708, whether the device has been switched into a manual mode is detected. If it is detected that the device has been switched into a manual mode, the output $FiO_2$ value is set to be equal to the $FiO_2$ value selected by a user (e.g., a bedside staff).

In S1710, the control process determines whether one or a plurality of alarms need to be triggered, and controls the alarm(s) accordingly. The exemplary process as illustrated in FIG. 10 (as described before) may be adopted by S1710.

In FIG. 12, after S1204, the determined $FiO_2$ value is then set as the output and sent to the output unit (S1206), and the control process updates the display to reflect the updated data (S1208), e.g., displaying data including the received input $SpO_2$ and the updated outputs.

After updating the display, the control process detects whether a user input has been detected which instructs exiting the automated control (S1210). If not, the control process proceeds to S1202 again to repeat the steps S1202 to S1210. If a user input has been detected instructing exiting the automated control, the control process ends.

Further, although the method of automatically controlling inspired oxygen delivery in some embodiments as described hereinbefore is performed by a controlling apparatus 10, the method can also be performed in the form of software; hardware; firmware; some combination of software, hardware, and/or firmware; and/or other mechanisms. For example, the method can be performed by a computer or microcomputer executing steps in machine-readable code, e.g., generated using coding tools. The software may also be integrated or installed in a controlling device, an oximeter, or a respiratory support device. The signals described herein are electronic signals, and the stored values are stored in non-transient electronically accessible storage.

Described herein is an apparatus for automatically controlling inspired oxygen delivery.

The apparatus includes: an input unit, receiving signals representing a plurality of input oxygen saturation ($SpO_2$) values for a patient; a memory, recording the received input $SpO_2$ values; a controller, determining output inspired oxygen concentration ($FiO_2$) values based on the input $SpO_2$ values; and an output unit, outputting the determined output $FiO_2$ values.

The controller generates control values based on the input $SpO_2$ values and a target $SpO_2$ value; and generates the output $FiO_2$ values based on the control values and reference inspired oxygen concentration ($rFiO_2$) values. As previously described, the control values include: immediate control values, generated based on the input $SpO_2$ values, the target $SpO_2$ value, and an immediate gain coefficient; accumulation control values, generated based on the input $SpO_2$ values, the target $SpO_2$ value, and an accumulation gain coefficient; and predictive control values, generated based on the input $SpO_2$ values, the target $SpO_2$ value, and a predictive gain coefficient; wherein the immediate gain coefficient is determined based on the $rFiO_2$ value; and wherein a non-linear compensation weighting is applied to the accumulation control value based on a predetermined non-linear relationship between partial pressure of arterial oxygen ($PaO_2$) and $SpO_2$.

For example, the apparatus may have a configuration as the controlling apparatus 10, as shown in FIG. 2.

Described herein is a system for automatically controlling inspired oxygen delivery. The system includes: one or a plurality of oxygen saturation monitoring devices, and one or a plurality of inspired oxygen control devices; a controlling device; and a network, enabling communication between the one or a plurality of oxygen saturation monitoring devices and the controlling device, and communication between the one or a plurality of inspired oxygen control devices and the controlling device.

The controlling device controls inspired oxygen delivery by: receiving signals representing a plurality of input oxygen saturation ($SpO_2$) values for a patient from each of the one or a plurality of oxygen saturation monitoring devices through the network; generating control values based on the input $SpO_2$ values and a target $SpO_2$ value; generating output inspired oxygen concentration ($FiO_2$) values based on the control values and reference inspired oxygen concentration ($rFiO_2$) values; and sending the determined output $FiO_2$ values to a corresponding inspired oxygen control device through the network. As previously described, the control values include: immediate control values, generated based on the input $SpO_2$ values, the target $SpO_2$ value, and an immediate gain coefficient; accumulation control values, generated based on the input $SpO_2$ values, the target $SpO_2$ value, and an accumulation gain coefficient; and predictive control values, generated based on the input $SpO_2$ values, the target $SpO_2$ value, and a predictive gain coefficient; wherein the immediate gain coefficient is determined based on the $rFiO_2$ value; and wherein a non-linear compensation weighting is applied to the accumulation control value based on a predetermined non-linear relationship between partial pressure of arterial oxygen ($PaO_2$) and $SpO_2$.

In this way, the controlling device may be used in a network with one or more pairs of oxygen saturation monitoring devices and inspired oxygen control devices connected to the network. This may allow real-time automatic control of performance at remote sites, and may allow collection of data on a large scale. A centralised controlling device may also simplify the adjustment or modification of the controlling process.

EXAMPLES

Described below are exemplary experiments involving methods for automatically controlling inspired oxygen delivery, and the corresponding experimental results.

First Example

Method

In a first example, a proportional-integral-derivative (PID) controller was enhanced by (i) compensation for the non-linear $SpO_2$—$PaO_2$ relationship, (ii) adaptation to the severity of lung dysfunction, and (iii) error attenuation within the target range.

The oxygen controller method was embodied in a stand-alone device consisting of a processing platform (laptop computer), device inputs and outputs, a servo-controlled air-oxygen blender and a user-interface displayed on the computer screen. The controlling instructions were written in a graphical programming language (LabVIEW 2010, National Instruments, Austin, USA) and uploaded in the laptop computer as machine-readable instructions.

The instructions provided a proportional-integral-derivative (PID) controller. For PID control, an error is defined as the deviation of the process signal from the set-point, and the value of the manipulated signal output at each moment is proportional to the error, its integral and its derivative, with a different multiplying coefficient in each case ($K_p$, $K_i$, $K_d$). In this case the error (e) was the numerical difference between the incoming value for $SpO_2$ (assuming a valid signal) and the midpoint of the selected target range (e.g. target range 91-95%, mid-point 93%). The integrand ($\int e \, d\tau$) was the sum of all errors (subject to constraints outlined below); the integral term in PID control lends the advantage of overcoming steady state error. The derivative $$\left(\frac{de}{dt}\right)$$

was the $SpO_2$ slope by linear regression over the previous 5 seconds, and in PID control gives a prediction of future error. The output of the process at each iteration was $\Delta FiO_2$, being the sum of each of the PID terms (Equation 4). The $FiO_2$ to be delivered (set $FiO_2$) was the sum of $\Delta FiO_2$ and a reference $FiO_2$ value ($rFiO_2$), a representation of the current baseline oxygen requirement (Equation 5). Set $FiO_2$ was rounded to ±0.5% and coerced to a value between 21 and 100%.

$$\Delta FiO_2 = K_p \cdot e + K_i \cdot \int e \, d\tau + K_d \cdot \frac{de}{dt} \qquad \text{(Equation 4)}$$

$$\text{Set } FiO_2 = \Delta FiO_2 + rFiO_2 \qquad \text{(Equation 5)}$$

The PID controlling process was within a loop iterating each second, allowing $FiO_2$ alterations to be made at 1 second intervals if necessary. Value ranges for $K_p$, $K_i$ and $K_d$ were derived from extensive simulation studies. The values of $K_p$, $K_i$ and $K_d$ used in the example were: $K_p$–1; $K_i$–0.0125; $K_d$–1. The value of $K_p$ could be adapted to the severity of lung dysfunction, within the range between –0.5 and –1 (see below).

Modifications of the PID controller were applied to accommodate some idiosyncrasies of the system under control. The error related to $SpO_2$ values within the target range was reduced by applying a fractional multiplier proportional to distance from the mid-point of the target range (target range attenuation). Further, given the relative imprecision of $SpO_2$ monitoring at values less than 80%, negative error was capped at 13%. These error adjustments were applied to calculation of the proportional term only.

Figure 19:
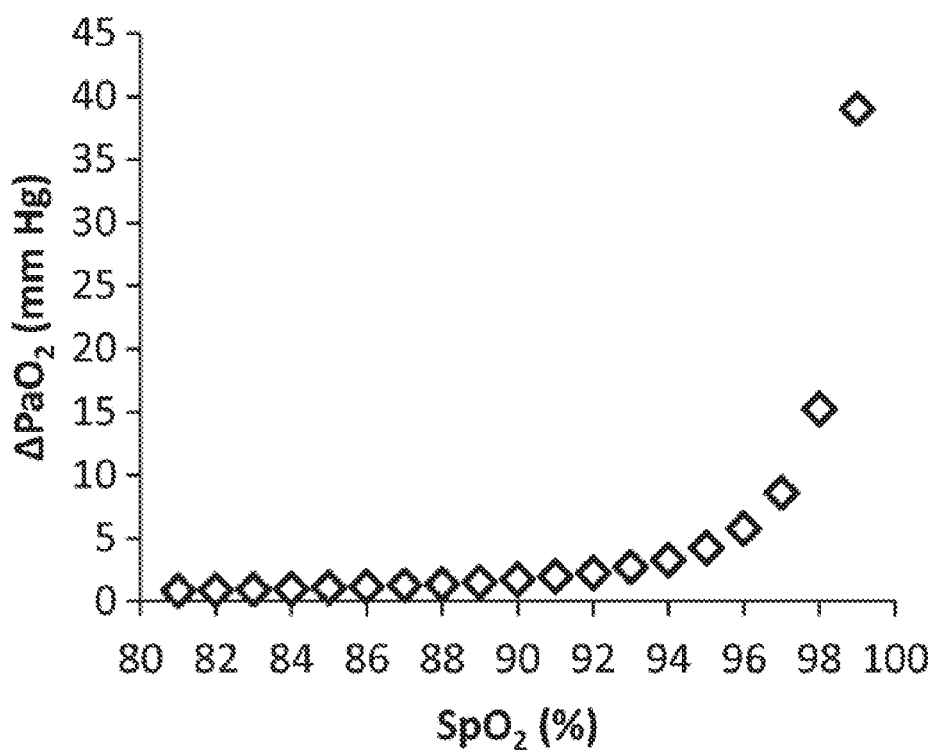
FIG. 19 is a graph of a relationship between PaO2 error and unitary $SpO_2$ error.

Some modifications to handling of the integral term were also implemented. In recognition that the integral term progressively increments $FiO_2$ in the event of unremitting hypoxia, its magnitude was capped so as to limit the maximum $\Delta FiO_2$ to 40% above $rFiO_2$. In hyperoxia ($SpO_2$ above target range when in supplemental oxygen), which can follow a hypoxic event as an "overshoot", the error at high $SpO_2$ values is not proportional to the likely deviation of $PaO_2$ from an acceptable value (FIG. 19).

To overcome this, Severinghaus compensation was adopted, whereby during hyperoxia, for as long as the integral term remained positive (i.e., tending to increase $\Delta FiO_2$), an error multiplier was applied to incoming positive errors (see Table 2 below). In determination of the integral term, the error multiplier was applied to positive $SpO_2$ errors until the integral term was reduced to zero. Values for the error multiplier were derived from the Severinghaus equation. When in room air, sequential values of $SpO_2$ above the target range were no longer considered to represent unremitting hyperoxia, and the integral term was not altered.

TABLE 2

Error multiplier for positive $SpO_2$ errors

| $SpO_2$ value | | | | | | | | |
|---|---|---|---|---|---|---|---|---|
| 92% | 93% | 94% | 95% | 96% | 97% | 98% | 99% | 100% |
| Error multiplier 1.2 | 1.4 | 1.7 | 2.2 | 2.9 | 4.4 | 7.9 | 20.1 | 50 |

The derivative term calculation was also modified in hyperoxia, such that negative $SpO_2$ slope was nullified (i.e. rendered=0) if all of the latest 5 $SpO_2$ values were above the set-point. Upward pressure on $\Delta FiO_2$ by the derivative term was thus avoided in hyperoxia.

An adaptive approach was investigated in which $K_p$ was modified according to the severity of lung dysfunction by applying a scaling factor proportional to current $rFiO_2$. The $K_p$ modification was by multiplication of the standing value of $K_p$ by a factor in the range 0.5 to 1.0 for $rFiO_2$ in the corresponding range 21% to 40%. Adaptation of $K_p$ in this way acknowledges the inverse proportional relationship between gain and severity of lung disease that has been observed in this population.

The primary input to the controlling process, $SpO_2$, can be sourced from any oximeter having an analogue or digital data output. For the pre-clinical testing, $SpO_2$ was derived from a simulation of oxygenation in the preterm infant. The output from the controlling process can be transmitted to any device that can receive and execute a desired value of $FiO_2$, including air-oxygen blenders and mechanical ventilators. For pre-clinical testing, the output $FiO_2$ was linked to the oxygenation simulator.

Preclinical Testing

The contribution of three enhancing features was investigated. The performance of all permutations of the PID control with a) Severinghaus compensation, b) $K_p$ adaptation and c) target range attenuation was evaluated using a simulation of oxygenation. A 1 Hz recording of $FiO_2$ and $SpO_2$ (~24 h duration) from each of 16 preterm infants on continuous positive airway pressure was converted to a series of values for ventilation-perfusion (V/Q) ratio and shunt. $SpO_2$ averaging time of the original recordings was 2-4 seconds, and was not averaged further during the data abstraction and simulation. The V/Q and shunt series was then linked to the controller under test within the automated oxygen controller, allowing a sequence of unique values for $SpO_2$ to be generated. The $SpO_2$ target range was set at 91-95%. Function of the controller without an integral term (i.e., proportional-derivative, PD), and of the fully-enhanced controller with a 30 sec lockout after an $FiO_2$ adjustment, were also examined. For these latter analyses, multiple permutations of PID coefficients were trialled in an attempt to optimise performance.

For each of the 16 $SpO_2$ sequences generated during simulation, proportions of time in the following oxygenation states were calculated: $SpO_2$ in target range, eupoxia ($SpO_2$ in target range, or above target range when in room air), $SpO_2$<80%, <85%, below and above target range, >96% in oxygen, and >98% in oxygen. Frequency of prolonged episodes of hypoxia ($SpO_2$<85%) and hyperoxia ($SpO_2$>96% in oxygen) were identified, as was frequency of $SpO_2$ overshoot, defined as $SpO_2$ readings above the target range for at least 60 sec over the 2 minutes following a hypoxic event with $SpO_2$<85%. $SpO_2$ instability was evaluated using $SpO_2$ coefficient of variation (CV), and frequency and mean duration of episodes outside the target range. These data were summarised as median and interquartile range (IQR), other than for $SpO_2$ overshoot, where data were pooled and expressed as a single value for each controlling process. Controlling performance was evaluated by comparison of medians using Friedman non-parametric repeated measures ANOVA with Dunn's post hoc test). For simplicity the comparisons were limited to the following groupings: a) PID with or without one enhancing factor (Severinghaus compensation/$K_p$ adaptation/target range attenuation); b) enhanced PID with or without subtraction of one enhancing factor; c) comparison of PID/enhanced PID/PID with 30 sec lockout/PD. Summary data regarding $SpO_2$ targeting by manual control from the original recordings were also generated, but statistical comparisons not made given the different $SpO_2$ target range (88-92%).

Results

The recordings using in the simulation came from 16 preterm infants of median gestation at birth 30.5 weeks (IQR 27.5-31 weeks), birth weight 1320 (910-1860) grams and post-natal age 2.0 (0-5.3) days. The infants had a considerable degree of $SpO_2$ instability, with hypoxic episodes ($SpO_2$<80) occurring with a frequency of 3.1 (1.6-9.9) episodes per 4 hours. At the time of the recording, CPAP pressure level was 7.0 (6.5-8.0) cm $H_2O$ and baseline $FiO_2$ 0.28 (0.25-0.31), with a baseline $FiO_2$ range of 0.21 to 0.61. After removal of missing $SpO_2$ data, the recordings were of duration 22 (20-26) hours.

In simulation testing, the complementary function of the different components of the PID controller was evident. Separate addition of $K_p$ adaptation and target range attenuation to the PID controller improved eupoxia time, whereas addition of Severinghaus compensation decreased episodes of hyperoxia (Table 3 and 4). Overall, the performance of the PID controller with all 3 enhancements was superior to other combinations. Without target range attenuation, eupoxia time trended higher than for fully enhanced PID (Table 3). Hypoxic and hyperoxic episodes were most effectively eliminated without $K_p$ adaptation (Table 4). Removal of Severinghaus compensation from the enhanced controller minimised hypoxia, but predictably led to more time in, and episodes of, hyperoxia (Tables 3 and 4). The enhanced controller performed better in all respects than an controller with a 30 second lockout period after each $FiO_2$ alteration, and considerably better than a PD controller (Tables 3 and 4).

Stability of the $SpO_2$ recording also varied considerably with different permutations of enhancing features (Table 5). The $SpO_2$ CV values in the recordings overall reflected the instability seen in individual examples (e.g., with $K_p$ adaptation removed from the enhanced controller). SpO$_2$ CV was minimised with the enhanced controller (and several other combinations) suggesting relative stability under these circumstances. Both PID control with a 30 second lockout and PD control resulted in less SpO$_2$ stability, with longer-lasting episodes above and below the target range (Table 5).

Separate addition of each enhancing feature to the PID controller showed a benefit. The enhanced controller had better all-round performance than PID controller with fewer enhancements, with an optimal combination of time in the desired SpO$_2$ range and avoidance of hypoxia and hyperoxia. This controller performed better than one with a 30 second lockout, and considerably better than PD control.

The enhanced PID controller was able to respond rapidly to SpO$_2$ deviations, adjusting FiO$_2$ up to once per second if necessary. The initial response to a hypoxic or hyperoxic event was largely the domain of the proportional and derivative terms, with further and more tempered FiO$_2$ adjustments dictated by the integral term until normoxia was restored.

At least in simulation, the enhanced PID controller was very effective in mitigation of episodes of prolonged hypoxia and hyperoxia. The addition of Severinghaus compensation to the PID controller was instrumental in overcoming hyperoxic events (including overshoot), and removing it from the enhanced controller resulted in their reappearance.

To sum up, in the above preclinical testing using an oxygenation simulation, the enhanced controller was very effective in targeting the desired SpO$_2$ range and avoiding the extremes of oxygenation.

TABLE 3

| | SpO$_2$ targeting | | | |
|---|---|---|---|---|
| | SpO$_2$ in target range | Eupoxia | SpO$_2$ <80% | SpO$_2$ <85% |
| Manual control (original recordings) | 49.2 (39.3-54.1) | 55.6 (51.3-65.1) | 0.60 (0.13-2.0) | 3.0 (2.0-6.4) |
| Core PID | 91.1 (83.1-92.6)$^{a,i}$ | 92.6 (90.9-94.0)$^{a,h,i}$ | 0.059 (0.022-0.12)$^g$ | 0.22 (0.13-0.43)$^g$ |
| Core PID + SC | 82.9 (78.3-89.8)$^c$ | 90.0 (83.9-92.9)$^a$ | 0.56 (0.15-2.6)$^a$ | 1.2 (0.55-4.2)$^a$ |
| Core PID + adaptive Kp | 92.2 (85.3-95.1)$^{b,d}$ | 94.7 (92.2-95.7)$^b$ | 0.040 (0.014-0.12)$^b$ | 0.20 (0.088-0.26)$^b$ |
| Core PID + TRA | 91.7 (85.1-94.5)$^d$ | 93.8 (91.8-95.5)$^b$ | 0.049 (0.019-0.11)$^b$ | 0.20 (0.10-0.30)$^b$ |
| Enhanced PID − SC | 91.7 (84.4-94.9)$^e$ | 94.3 (91.7-95.5)$^d$ | 0.037 (0.017-0.11)$^c$ | 0.20 (0.091-0.26)$^c$ |
| Enhanced PID − adaptive Kp | 88.1 (82.3-92.2)$^g$ | 92.5 (89.5-95.2)$^d$ | 0.43 (0.076-1.3)$^d$ | 0.75 (0.23-1.8)$^d$ |
| Enhanced PID − TRA | 91.4 (86.2-95.6)$^{j,h}$ | 95.5 (93.3-95.9)$^c$ | 0.094 (0.028-0.25)$^d$ | 0.28 (0.18-0.66) |
| Enhanced PID | 91.2 (85.3-95.5)$^{h,i}$ | 95.1 (92.9-96.5)$^g$ | 0.088 (0.024-0.18)$^{d,g}$ | 0.24 (0.094-0.43)$^g$ |
| Enhanced PID 30 sec lockout | 87.9 (81.3-93.3)$^{j,k}$ | 92.5 (90.1-94.0)$^{h,i}$ | 0.21 (0.13-0.40)$^h$ | 0.51 (0.30-0.73)$^h$ |
| PD control | 52.7 (38.6-55.5)$^{j,l}$ | 52.8 (38.6-59.1)$^{h,j}$ | 1.6 (0.24-8.4)$^h$ | 4.4 (0.67-17)$^h$ |

| | SpO$_2$ below target range | SpO$_2$ above target range | SpO$_2$ >96% in oxygen | SpO$_2$ >98% in oxygen |
|---|---|---|---|---|
| Manual control (original recordings) | 10 (7.2-17) | 38 (32-54) | 3.3 (2.3-4.6) | 0.30 (0.16-0.83) |
| Core PID | 3.7 (3.1-4.2)$^{a,i}$ | 4.8 (3.9-13)$^{a,f}$ | 1.73 (1.0-2.1)$^h$ | 0.070 (0.030-0.12)$^g$ |
| Core PID + SC | 6.2 (4.5-10)$^c$ | 6.9 (4.5-13) | 1.5 (0.63-3.0) | 0.10 (0.016-0.51) |
| Core PID + adaptive Kp | 2.6 (2.0-3.8)$^{b,d}$ | 4.4 (2.6-12)$^b$ | 1.1 (0.87-1.8) | 0.089 (0.0077-0.19) |
| Core PID + TRA | 2.9 (2.0-3.9)$^d$ | 4.6 (2.8-13) | 1.2 (0.87-1.7) | 0.047 (0.019-0.11) |
| Enhanced PID − SC | 2.8 (2.1-4.1)$^e$ | 4.6 (2.7-12)$^c$ | 1.1 (0.88-1.8)$^c$ | 0.092 (0.011-0.20)$^{d,f}$ |
| Enhanced PID − adaptive Kp | 5.1 (3.5-6.9)$^{f,g}$ | 4.9 (3.1-12)$^c$ | 1.2 (0.51-1.7) | 0.088 (0.014-0.23)$^d$ |
| Enhanced PID − TRA | 3.6 (2.8-4.9)$^h$ | 3.0 (1.3-12)$^d$ | 0.44 (0.25-0.63)$^d$ | 0.013 (0-0.042)$^e$ |
| Enhanced PID | 3.8 (2.6-5.0)$^{f,i}$ | 3.2 (1.2-12)$^{d,e}$ | 0.31 (0.22-0.56)$^{d,g}$ | 0.013 (0-0.042)$^{c,h}$ |

TABLE 3-continued

| | SpO$_2$ targeting | | | |
|---|---|---|---|---|
| Enhanced PID 30 sec lockout | 5.5 (4.1-6.8)$^j$ | 4.8 (1.9-12) | 0.76 (0.45-1.2)$^h$ | 0.024 (0-0.11) |
| PD control | 20 (6.3-44)$^j$ | 12 (4.2-39)$^f$ | 2.5 (0.51-20)$^h$ | 0 (0-0.037)$^h$ |

Comparison of proportion of time (% of total time) within pre-specified SpO$_2$ ranges.
Median (interquartile range).
Within-column statistical comparisons (Friedman ANOVA with Dunn's post hoc test):
$^a$Differs from $^b$, P < 0.05,
$^c$Differs from $^d$;
$^e$Differs from $^f$;
$^g$Differs from $^h$;
$^i$Differs from $^j$;
$^k$Differs from $^l$.
PID: proportional-integral-derivative;
Kp: proportional coefficient;
SC: Severinghaus compensation,
TRA: target range attenuation.

TABLE 4

| | Hypoxic and hyperoxic episodes and overshoot | | | | |
|---|---|---|---|---|---|
| | Hypoxia SpO$_2$ <85% | | Hyperoxia SpO$_2$ >96% in oxygen | | Post-hypoxia overshoot |
| | 30 sec episodes per 24 h | 60 sec episodes per 24 h | 30 sec episodes per 24 h | 60 sec episodes per 24 h | Episodes per 24 h* |
| Manual control (original recordings) | 30 (12-55) | 8.0 (5.7-18) | 23 (17-30) | 10 (6.5-14) | 0.71 |
| Core PID | 0 (0-1.2)$^h$ | 0 (0-0.82) | 5.0 (3.1-6.8)$^{b,c,h}$ | 2.2 (0.84-3.4)$^{b,h}$ | 0.90 |
| Core PID + SC | 0 (0-1.2) | 0 (0-0.21) | 0 (0-0.62)$^a$ | 0 (0-0)$^a$ | 0.19 |
| Core PID + adaptive Kp | 0 (0-1.4) | 0 (0-0) | 6.5 (5.5-11)$^{b,d}$ | 2.7 (1.7-5.4)$^b$ | 0.90 |
| Core PID + TRA | 0 (0-1.2) | 0 (0-0.20) | 5.5 (3.1-6.2)$^b$ | 1.7 (0.84-3.4)$^b$ | 0.84 |
| Enhanced PID – SC | 0 (0-1.9) | 0 (0-0) | 6.5 (5.5-11)$^e$ | 2.3 (1.7-5.4)$^e$ | 1.0 |
| Enhanced PID – adaptive K$_p$ | 0 (0-0.053) | 0 (0-0.0086) | 0 (0-0.026)$^f$ | 0 (0-0)$^f$ | 0.19 |
| Enhanced PID – TRA | 0 (0-2.1) | 0 (0-0) | 1.1 (0.62-1.2)$^f$ | 0 (0-0)$^f$ | 0.13 |
| Enhanced PID | 0 (0-1.9)$^h$ | 0 (0-0)$^h$ | 1.0 (0-1.6)$^{f,g}$ | 0 (0-0)$^{f,g}$ | 0.19 |
| Enhanced PID 30 sec lockout* | 0.47 (0-2.2) | 0 (0-0)$^h$ | 2.4 (1.8-5.6) | 0 (0-0.14)$^g$ | 0.45 |
| PD control* | 4.8 (2.2-17)$^g$ | 2 (0-4.2)$^g$ | 12 (0-110)$^h$ | 5.5 (0-54)$^h$ | 0.13 |

Comparison of frequency of continuous hypoxic and hyperoxic episodes (≥30 and ≥60 sec duration) and of overshoot. Within-column statistical comparisons (Friedman ANOVA with Dunn's post hoc test):
$^a$Differs from b, P < 0.05,
$^c$Differs from d;
$^e$Differs from f;
$^g$Differs from h;
*data for overshoot episodes pooled for all 16 recordings. Abbreviations as per Table 3; see Methods hereinbefore for definition of overshoot.

TABLE 5

| | SpO$_2$ instability | | | | |
|---|---|---|---|---|---|
| | SpO$_2$ coefficient of variation (%) | SpO$_2$ <91% (episodes/h) | SpO$_2$ <91% (episode duration, sec) | SpO$_2$ >95% (episodes/h) | SpO$_2$ >95% (episode duration, sec) |
| Manual control (original recordings) | 4.2 (3.3-4.8) | n.a. | n.a. | n.a. | n.a. |
| Core PID | 1.8 (1.7-2.3)$^g$ | 16 (14-19)$^{a,h}$ | 7.9 (7.2-8.8)$^{a,e}$ | 17 (14-28)$^{a,i}$ | 11 (9.4-21)$^{a,g}$ |
| Core PID + SC | 2.9 (2.3-5.4)$^a$ | 24 (19-40)$^c$ | 9.1 (8.2-9.3) | 27 (18-30)$^c$ | 9.2 (8.6-20)$^c$ |
| Core PID + adaptive Kp | 1.7 (1.5-2.1)$^b$ | 10 (7.7-12)$^{b,d}$ | 9.2 (8.7-11)$^b$ | 13 (7.1-17)$^{b,d}$ | 16 (13-25)$^{b,d}$ |

TABLE 5-continued

| | SpO$_2$ instability | | | | |
|---|---|---|---|---|---|
| | SpO$_2$ coefficient of variation (%) | SpO$_2$ <91% (episodes/h) | SpO$_2$ <91% (episode duration, sec) | SpO$_2$ >95% (episodes/h) | SpO$_2$ >95% (episode duration, sec) |
| Core PID + TRA | 1.7 (1.6-2.2)$^b$ | 13 (9.6-14)$^d$ | 8.9 (8.2-9.6)$^b$ | 15 (9.5-24)$^d$ | 13 (11-25)$^d$ |
| Enhanced PID – SC | 1.7 (1.5-2.1) | 11 (8.0-13)$^e$ | 9.7 (9.0-11)$^d$ | 13 (7.3-18)$^g$ | 15 (13-26)$^e$ |
| Enhanced PID – adaptive Kp | 2.7 (1.8-3.8)$^c$ | 18 (15-25)$^f$ | 9.4 (8.9-10) | 17 (13-25)$^e$ | 9.7 (8.7-23)$^f$ |
| Enhanced PID – TRA | 1.8 (1.6-2.4)$^d$ | 13 (11-16)$^f$ | 9.2 (8.7-10)$^c$ | 11 (5.3-17)$^f$ | 9.3 (8.3-24)$^f$ |
| Enhanced PID | 1.7 (1.6-2.3)$^g$ | 13 (11-15)$^{f,g}$ | 9.7 (9.0-11)$^{d,g}$ | 12 (5.2-15)$^{f,h,j}$ | 9.7 (8.6-26)$^{f,g}$ |
| Enhanced PID 30 sec lockout | 2.2 (2.0-2.8)$^h$ | 15 (12-17) | 13 (12-15)$^{f,h}$ | 13 (5.8-16)$^j$ | 14 (12-29)$^h$ |
| PD control | 4.5 (3.0-7.4)$^h$ | 27 (14-56)$^h$ | 21 (17-27)$^{f,h}$ | 15 (7.1-36) | 28 (11-42)$^h$ |

Indices of SpO$_2$ instability.
Median (interquartile range).
Within-column statistical comparisons (Friedman ANOVA with Dunn's post hoc test):
$^a$Differs from b, $P < 0.05$,
$^c$Differs from d;
$^e$Differs from f;
$^g$Differs from h;
$^i$Differs from j.
PID: proportional-integral-derivative;
Kp: proportional coefficient;
SC: Severinghaus compensation;
TRA: target range attenuation.

Second Example

Method

In a second example, the enhanced PID controller of Example 1 was incorporated in an oxygen control device, and tested by clinical evaluation.

Figure 20:
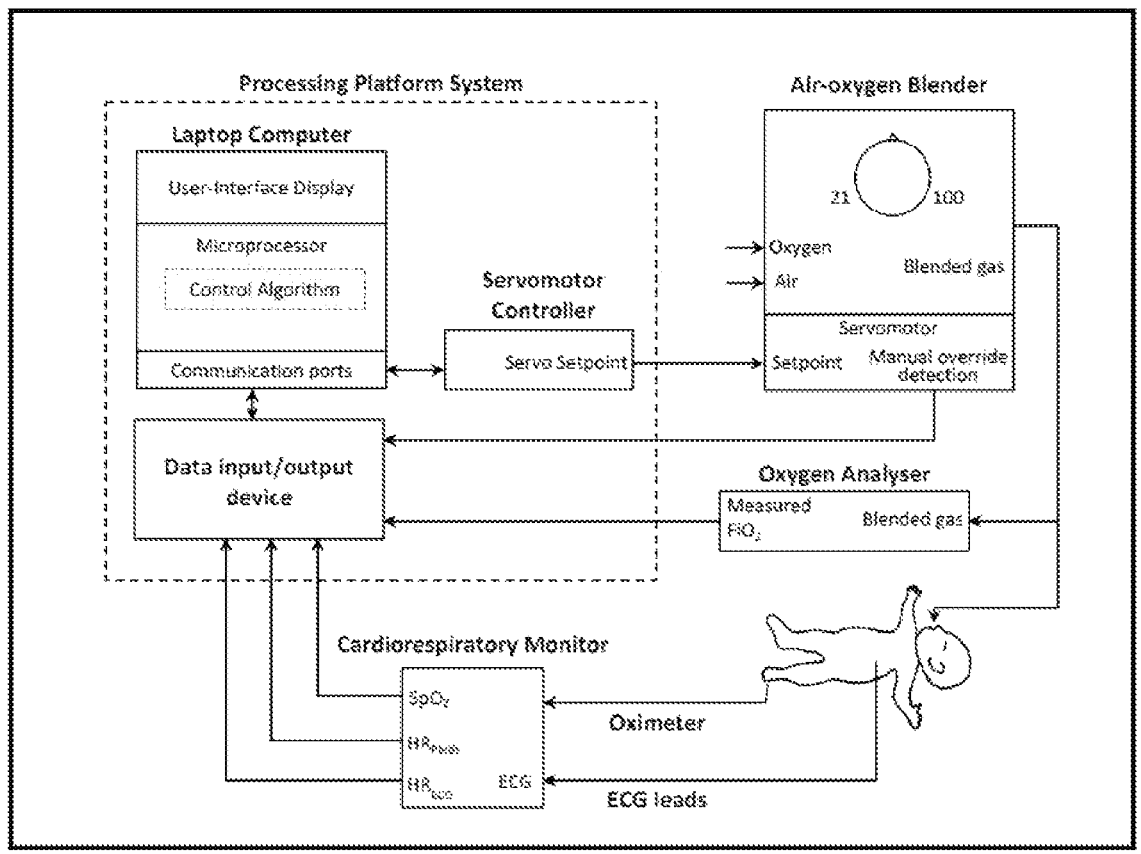
FIG. 20 is a block diagram of an inspired oxygen delivery system used in the second exemplary experiment.

As illustrated in FIG. 20, the device incorporating the method for automated oxygen control was a standalone instrument consisting of a laptop computer, an automated air-oxygen blender and a data input/output device (USB-6008, National Instruments, Austin, USA) incorporating an analogue-digital (AD) converter. The controller received digital inputs from a standard cardiorespiratory monitor (Drager Infinity, Drager Medical Systems Inc, Notting Hill, Australia), including SpO$_2$ (Masimo oximetry probe, Masimo Corp, Irvine, Calif.), heart rate determined from the electrocardiographic signal (HR$_{ecg}$), and plethysmographic heart rate (HR$_{pleth}$). SpO$_2$ averaging was set at fast (2-4 sec). FiO$_2$ was measured via a sensor in the proximal limb of the respiratory circuit (Teledyne), and input to the device via the AD converter. The desired value for FiO$_2$ derived from the controller was routed to a servomotor (model HS-322HD, Hitec RCD USA, Poway, USA) custom-mounted on an air-oxygen blender (Bird Ultrablender, Carefusion, Seven Hills, NSW), which allowed automatic rotation of the blender FiO$_2$ selection dial via a ringed gearing mechanism. The servomotor and gearing system had sufficient torque and precision to allow small adjustments to FiO$_2$ (minimum±0.5%) to be made accurately and repeatedly. The servomotor also had a low holding torque such that the blender dial could still be turned manually; such manual intervention was detected by a position sensor and resulted in a switch to a manual mode in which FiO$_2$ was no longer under automated control (see below). At the beginning of each study, the servomotor calibration was checked and if necessary altered.

The automated control method consisted of a PID controlling process with enhancements in the determination of the proportional, integral and derivative terms to suit application of PID control to automated oxygen control in the preterm infant. The enhancements of the proportional term included modulation based on severity of lung dysfunction, error attenuation while within the target range and error capping during hypoxia. Integral term enhancements included integrand magnitude capping, compensation for the non-linear PaO$_2$-SpO$_2$ relationship, and inhibition of integrand increase in room air.

The PID controlling process was within a loop iterating each second. The method was thus designed to detect and respond to the rapid changes in oxygenation that are all-too-frequent in preterm infants. Value ranges for the PID coefficients were derived from extensive simulation studies using data from preterm infants, allowing multiple permutations of different values for all coefficients to be examined. The values of $K_p$, $K_i$ and $K_d$ used in the example were: $K_p$–1; $K_i$–0.0125; $K_d$–1. The value of $K_p$ could be adapted to the severity of lung dysfunction, within the range between –0.5 and –1.

Non-numeric SpO$_2$ values were treated as missing, as were SpO$_2$ values in which the values of HRecg and HRpleth differed by >30 bpm. In the event of missing SpO$_2$ values, the FiO$_2$ was held at the current value. Full function of the controller resumed as soon as a valid signal was recovered.

During automated control, bedside staff could over-ride the control device by manually turning the blender FiO$_2$ dial. This signalled manual over-ride through the detection of a discrepancy between the set FiO$_2$ and the FiO$_2$ value detected by the position sensor within the servomotor. Once in manual over-ride, automated control resumed at the user-selected FiO$_2$ 30 seconds after the last manual alteration to FiO$_2$. The device could also be locked in manual control mode by the research team on instruction from bedside staff if deemed necessary.

Clinical Testing

The study was conducted in the Neonatal and Paediatric Intensive Care Unit at the Royal Hobart Hospital. The Unit provides care for ~70 preterm infants <32 weeks gestation per year, and has an ethos of using non-invasive respiratory support whenever possible for this patient group, including continuous positive airway pressure (CPAP) and high flow nasal cannulae (HFNC). The $SpO_2$ target range for titration of oxygen therapy has been revised to 90-94%, having previously been 88-92%.

Preterm infants <37 weeks gestation and <4 months of age were eligible for study if on non-invasive respiratory support (CPAP or HFNC) and receiving supplemental oxygen at the outset of the study period. Infants with acute instability or congenital abnormalities (including cardiac malformations other than patent ductus arteriosus) were excluded.

This was a prospective interventional study of a 4 hour period of automated oxygen control, which was compared with two flanking periods of standard manual control totaling 8 hours (4 hours before and after automated control). There was a 15 min interval between study periods to avoid carryover effects. Study personnel were in attendance for the duration of the automated control period, but were not to interact with bedside clinical staff unless there was a critical system malfunction. During automated control, caregivers could over-ride the control device output to the customised air-oxygen blender used in the study by turning the blender dial. During the recordings of manual control, bedside caregivers were instructed to use their usual approach to $SpO_2$ targeting, with the standard $SpO_2$ target range (90-94%). Based on previous studies, it was expected that with manual control the upper end of this range would be preferentially targeted. Given that the automated controller targets the mid-point of the $SpO_2$ range, during automated control the target range was set at 91-95%, with the expectation that the manual and automated $SpO_2$ histograms would overlap, with a similar median $SpO_2$. For both manual and automated study epochs, the $SpO_2$ alarm settings were identical—lower limit 89%, upper limit 96%.

Prior to the study the oximetry probe was placed in a post-ductal position, and not moved during the 3 study epochs unless there was a clinical need or a consistently poor $SpO_2$ signal. Care times were scheduled to fall outside the data recording periods where possible. For automated control a constant value for reference $FiO_2$ ($rFiO_2$) was selected in each infant based on most recent basal supplemental oxygen requirements.

Relevant demographic and clinical data were recorded for each infant, including gestation, birth weight, and details of clinical state and level of respiratory support at the time of the study. $SpO_2$ and $FiO_2$ were recorded at 1 Hz during both manual and automated control. Analysis of these recordings allowed evaluation of $SpO_2$ instability in each infant, assessed by $SpO_2$ coefficient of variation, and number and mean duration of episodes outside the target range. Further, the proportion of time in each of the following oxygenation states was ascertained: $SpO_2$ in target range, eupoxia ($SpO_2$ in target range, or above target range in room air), $SpO_2$ in alarm range (89-96%), and $SpO_2$<80%, 80-84%, 85-88%, 97-98% in oxygen, and >98% in oxygen. For calculation of these values the denominator was usable time after exclusion of data during periods of missing $SpO_2$ signal. Frequency of prolonged episodes of hypoxia and hyperoxia were identified, as was frequency of $SpO_2$ overshoot, defined as $SpO_2$ readings above the target range for at least 60 sec over the 2 minutes following a hypoxic event with $SpO_2$<85%. The number of $FiO_2$ adjustments (change in measured $FiO_2$ by 1% or greater) during manual and automated recordings was determined, as was the average oxygen exposure (mean $FiO_2$) in each case.

Data were expressed as median and interquartile range (IQR) unless otherwise stated. Comparisons were made between automated and manual control epochs using Wilcoxon matched pairs test. For these analyses data from both manual control epochs were pooled, but additionally the best manual control epoch for each infant (i.e., the manual recording of duration >2 h with the greatest proportion of time in eupoxia) was also used as the comparator. The primary outcome was proportion of time in eupoxia. The chosen sample size for the study (20 infants) was primarily based around need to gain an initial clinical experience of controller performance and safety in a sufficient number of subjects. In a previous study of 45 infants we found proportion of time in the target range when in oxygen to be 30±15% (mean±SD). Assuming a similar standard deviation for the differences between paired automated and manual control values in the present study, a sample of 20 infants thus allowed detection of a 10% difference in eupoxia time between automated and manual epochs with 80% power and alpha error 0.05.

Results

The study was conducted from May to December 2015. Enrolled infants (n=20) were of median gestational age at birth 27.5 weeks (IQR 26-30 weeks) and birth weight 1130 (940-1400) gm. 15 of the 20 infants were male (75%). The infants were studied at a post-natal age of 8.0 (1.8-34) days, corrected gestational age of 31 (29-33) post-menstrual weeks, and body weight of 1400 (1120-1960) g. For infants studied on CPAP (n=13) the pressure level at the start of recording was 6 (5-8) cm $H_2O$; for those studied on HFNC (n=7), starting flow rate was 6 (5.5-6.5) L/min. Nurse:patient ratio was 1:2 in all cases.

Data from two flanking periods of manual control were available in 18 infants, with data logging failure and need for intubation immediately after automated control being the reasons for unavailability of a second manual control data recording (one case each). The proportion of missing signal was 2.9 (0.5-5.4)%, 1.7 (0.7-3.4)% and 1.5 (0.8-7.1)% in the first manual, automated and second manual recordings, respectively, leaving 3.8 (3.7-4.0), 3.8 (3.7-3.9) and 4.0 (3.8-4.0) hours of usable time for analysis.

Figure 21:
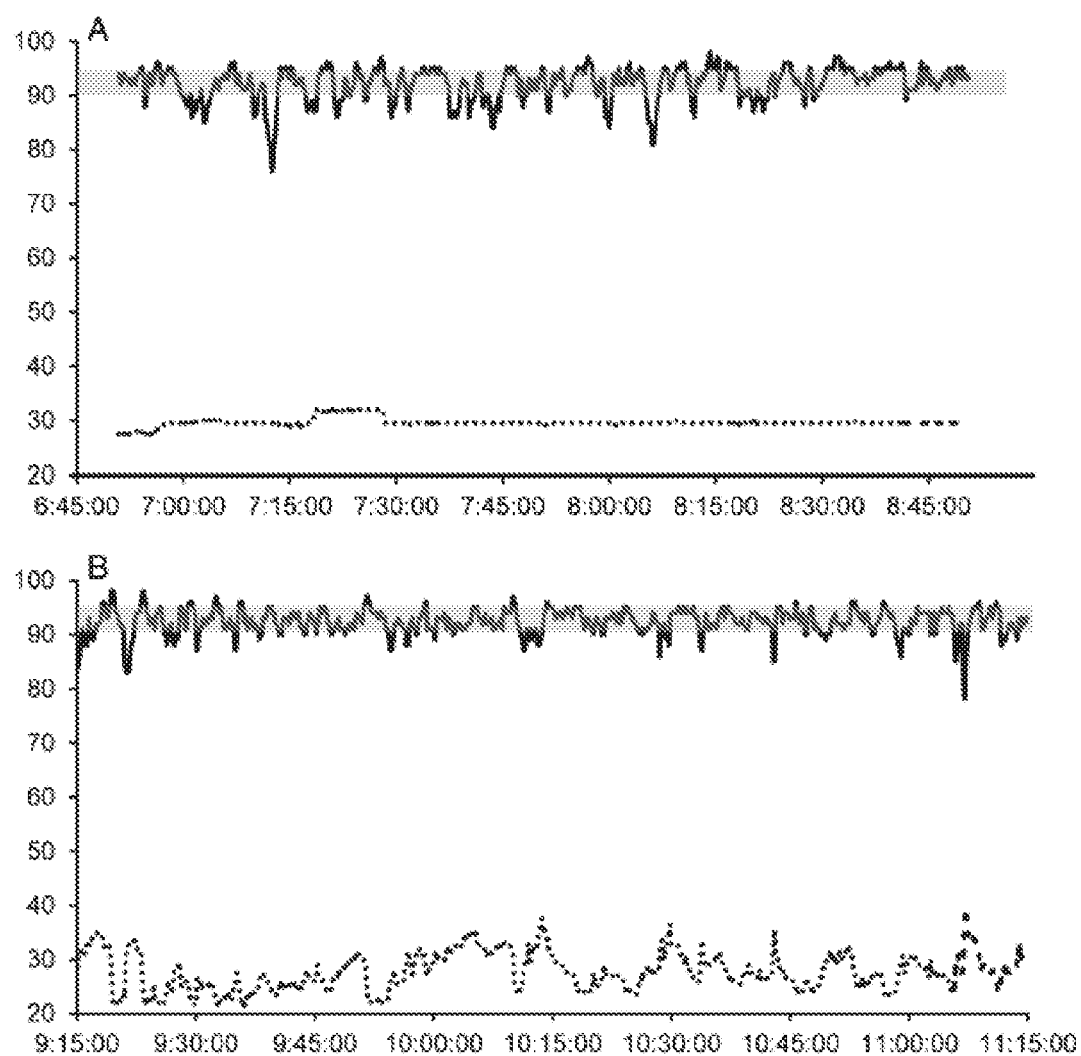
FIGS. 21A and 21B are graphs of two hour recordings from the same infant during manual and automated control recorded in the second exemplary experiment.

FIGS. 21A and 21B show two hour recordings from the same infant during manual and automated control, including sample recordings of $SpO_2$ (solid line, Y-axis: % saturation) and $FiO_2$ (dashed line, Y-axis: % oxygen) of:
  (A) Infant 5 born at 27 weeks gestation, studied on day 40, on high flow nasal cannulae (HFNC) 6 L/min, manual control, eupoxia time 59% (shown in FIG. 21A); and
  (B) Infant 5, automated control, eupoxia time 79%, with automated control with $rFiO_2$ set at 29% throughout, eupoxia time 82% (shown in FIG. 21B).

FIGS. 21A and 21B reveal the typical variability of $SpO_2$ during manual control of $FiO_2$ (FIG. 21A), which was less prominent during automated control (FIG. 21B). The exemplary data shown in FIGS. 21A and 21B demonstrate the rapid responses in $FiO_2$ made by the controller and the increase in time in the target range (as shown by the grey band).

Figure 22:
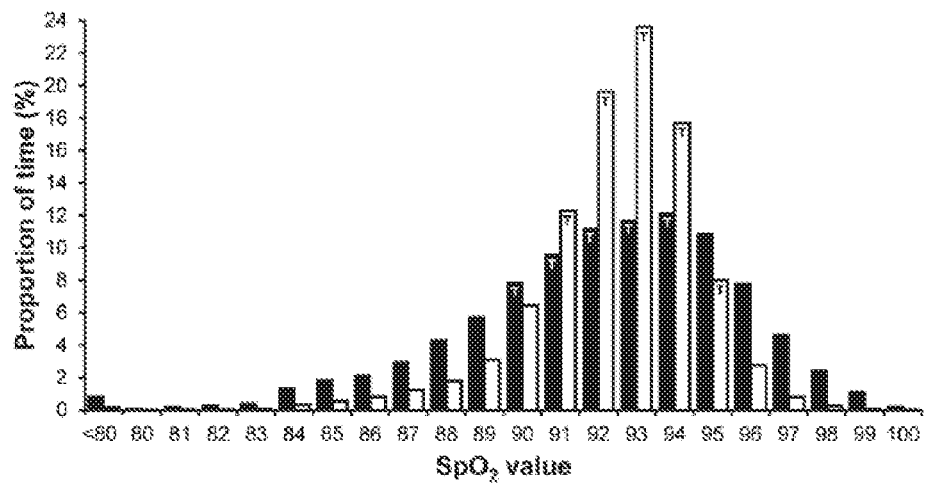
FIG. 22 is a graph of frequency histograms of pooled $SpO_2$ data according to the results of the second exemplary experiment.

As shown in FIG. 22 (black bars: manual control; white bars: automated control, T=$SpO_2$ values within target range, the target range being 90%-94% for manual control, 91%-

95% for automated control), frequency histograms of pooled $SpO_2$ data show a substantial increase in proportion of time within the target range with automated control, with both hypoxic and hyperoxic values under-represented compared with manual control. The $SpO_2$ targeting profile during manual control appeared having the peak of the curve at the upper end of the targeted range. By contrast, and as expected, automated control targeted the mid-point of the set target range (i.e. $SpO_2$ 93%). When receiving supplemental oxygen, median $SpO_2$ in pooled data was 93% for both manual and automated control.

Oxygenation was considerably more stable during automated control, with fewer $SpO_2$ deviations below target range and below 80%, and a shorter duration of all episodes outside target range compared with manual control. The $SpO_2$ coefficient of variation also differed considerably (manual: 3.8 (3.2-4.7)%, automated: 2.3 (1.8-3.0)%, P<0.0001).

Compared with both manual control epochs combined, automated control resulted in 23% and 25% more time in the target and eupoxic ranges, respectively (Table 6). Time spent within the alarm range (89-96%) was also higher. Automated control considerably diminished time at both extremes of oxygenation, virtually eliminating hypoxia with $SpO_2$<80% and hyperoxia in oxygen with $SpO_2$>98%. Time spent in the lesser ranges of hypoxia and hyperoxia was also reduced.

During manual control epochs, $FiO_2$ adjustments of at least 1% were made 2.3 (1.3-3.4) times per hour by bedside staff. During automated control, the minimum alteration to $FiO_2$ of 0.5% was being actuated by the servomotor frequently (9.9 alterations/min overall), and changes to measured $FiO_2$ of at least 1% occurred at a frequency of 64 (49-98) per h. When in automated control, a total of 18 manual adjustments were made in all 20 recordings (0.24 adjustments/h), a reduction by 90% from the rate of manual adjustments observed during manual control (2.3/h). The maximum number of manual adjustments in an individual subject during automated control was 4 in a 4 hour recording (i.e. 1/h). No critical system malfunctions occurred.

Median values for oxygen requirement (average $FiO_2$) were 27 (25-30)%, 27 (25-30)% and 26 (24-31)% for first manual, automated and second manual recordings, respectively. Oxygen requirements did not differ between automated and either manual recording (P>0.05, Wilcoxon matched pairs test).

In summary, the enhanced PID controller was considerably more effective in $SpO_2$ targeting than routine manual control, with 25% more time in the desired $SpO_2$ range. The extremes of oxygenation were largely avoided, and prolonged episodes of hypoxia and hyperoxia were virtually eliminated. Effective oxygen control was achieved with very few manual fraction of inspired oxygen adjustments, and similar exposure to oxygen.

TABLE 6

Oxygen saturation ($SpO_2$) targeting

|  | Manual control | Automated control | P value* |
|---|---|---|---|
| $SpO_2$ in target range | 55 (46-60)% | 78 (75-87)% | 0.0001 |
| $SpO_2$ below target range | 19 (12-27)% | 14 (7.8-19)% | 0.0027 |
| $SpO_2$ above target range | 25 (23-35)% | 5.1 (3.-6.9)% | 0.0003 |
| Eupoxia | 56 (48-63)% | 81 (76-90)% | <0.0001 |
| $SpO_2$ in alarm range (89-96%) | 81 (70-83)% | 93 (90-98)% | 0.0006 |
| $SpO_2$ in alarm range or higher when in air | 81 (73-83)% | 95 (92-98)% | <0.0001 |
| $SpO_2$ <80% | 0.7 (0.10-1.3)% | 0 (0-0.17)% | 0.0006 |
| $SpO_2$ 80-84% | 2.6 (1.2-3.2)% | 0.39 (0.10-0.67)% | 0.0001 |
| $SpO_2$ 85-88% | 10 (6.8-15)% | 3.5 (1.1-5.8)% | 0.0002 |
| $SpO_2$ 97-98% when in oxygen | 5.0 (3.2-7.9)% | 0.71 (0.28-1.5)% | 0.0001 |
| $SpO_2$ 99-100% when in oxygen | 0.46 (0.22-1.4)% | 0 (0-0.12)% | 0.0010 |

Comparison of proportion of time (% of total usable time) within pre-specified $SpO_2$ ranges for manual and automated control.
Manual control data pooled from two flanking periods.
Median (interquartile range).
*Wilcoxon matched pairs test.

These findings were mirrored in the analysis of prolonged episodes of hypoxia and iatrogenic hyperoxia, both of which occurred with modest frequency during manual control (Table 7), but were distinctly uncommon during automated control. No overshoot episodes were identified in any of the automated control recordings.

Figure 23:
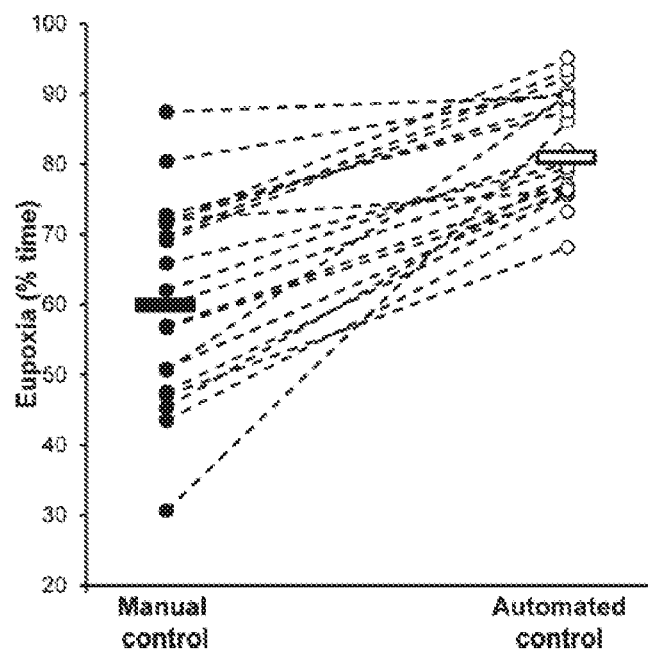
FIG. 23 is a graph comparing best manual control epoch with automated control according to the results of the second exemplary experiment.

As shown in FIG. 23 (individual paired values of time in eupoxia for the best manual control epoch compared with automated control; Horizontal bar=median; Eupoxia=$SpO_2$ in target range, or above target range when in room air), when measured against the best of the two manual control epochs, the apparent benefit of automated control persisted, with time in the eupoxic range being 60 (50-72)% and 81 (76-90)% for best manual and automated control, respectively (P<0.001). Moreover, automated control was associated with better $SpO_2$ targeting in each individual studied, with the relative improvement in eupoxia time ranging from 2.2 to 55% (FIG. 23).

TABLE 7

Hypoxic and hyperoxic episodes

|  | 30 second episodes | | | 60 second episodes | | |
|---|---|---|---|---|---|---|
|  | Manual control | Automated control | P value* | Manual control | Automated control | P value* |
| Hypoxia $SpO_2$ <80%, episodes/4 h | 1.0 (0-3.2) | 0 (0-0) | 0.0001 | 0.51 (0-0.76) | 0 (0-0) | 0.0010 |
| Hypoxia $SpO_2$ <85%, episodes/4 h | 5.6 (2.4-7.5) | 0 (0-1.1) | <0.0001 | 1.9 (0.62-2.6) | 0 (0-0) | 0.0001 |
| Hyperoxia $SpO_2$ >96% in oxygen, episodes/4 h | 8.5 (4.9-14) | 0 (0-0.25) | 0.0001 | 1.9 (1.0-3.7) | 0 (0-0) | 0.0001 |

TABLE 7-continued

Hypoxic and hyperoxic episodes

| | 30 second episodes | | | 60 second episodes | | |
|---|---|---|---|---|---|---|
| | Manual control | Automated control | P value* | Manual control | Automated control | P value* |
| Hyperoxia $SpO_2$ >98% in oxygen, episodes/4 h | 0.55 (0.37-2.4) | 0 (0-0) | 0.0021 | 0 (0-1.0) | 0 (0-0) | 0.049 |

Comparison of frequency of continuous hypoxic and hyperoxic episodes (30 and 60 sec duration) between manual and automated control.
Manual control data pooled from two flanking periods.
Median (interquartile range).
*Wilcoxon matched pairs test.

Many modifications will be apparent to those skilled in the art without departing from the scope of the present invention as hereinbefore described with reference to the accompanying drawings.

RELATED APPLICATIONS

The originally filed specification of the following related application is incorporated by reference herein in its entirety: Australian Provisional Patent Application 2015904621, filed 10 Nov. 2015.

The invention claimed is:

1. A method for automatically controlling inspired oxygen delivery, including:
   receiving, by a controlling apparatus, signals representing a plurality of input oxygen saturation ($SpO_2$) values for a patient;
   generating, by the controlling apparatus, control values based on the input $SpO_2$ values and a target $SpO_2$ value;
   generating, by the controlling apparatus, output inspired oxygen concentration ($FiO_2$) values based on the control values and reference inspired oxygen concentration ($rFiO_2$) values; and
   providing, by the controlling apparatus, the output $FiO_2$ values to a respiratory support device,
   wherein the control values include:
      immediate control values, generated based on the input $SpO_2$ values, the target $SpO_2$ value, and an immediate gain coefficient;
      accumulation control values, generated based on the input $SpO_2$ values, the target $SpO_2$ value, and an accumulation gain coefficient; and
      predictive control values, generated based on the input $SpO_2$ values, the target $SpO_2$ value, and a predictive gain coefficient;
   wherein the immediate control values are determined based on the $rFiO_2$ value; and
   wherein a non-linear compensation weighting is applied to the accumulation control values based on a predetermined non-linear relationship between partial pressure of arterial oxygen ($PaO_2$) and $SpO_2$.

2. The method of claim 1, further including:
   modifying, by the controlling apparatus, the accumulation control values to cap the control values at a selected maximum control value.

3. The method of claim 2, wherein each of the output $FiO_2$ values is the sum of the corresponding control value and the corresponding $rFiO_2$ value.

4. The method of claim 1, wherein the immediate gain coefficient is modified based on a performance evaluation result.

5. The method of claim 4, wherein the performance evaluation result is generated based on at least one of:
   a hypoxic time duration, in which the input $SpO_2$ values in the performance analysis time period were in a hypoxic range; and
   a hyperoxic time duration, in which the input $SpO_2$ values in the performance analysis time period were in a hyperoxic range.

6. The method of claim 4, further including:
   determining, by the controlling apparatus, a target $SpO_2$ range, wherein the target $SpO_2$ is within the $SpO_2$ range;
   wherein the performance evaluation result is generated based on at least one of:
   a target time duration, in which the input $SpO_2$ values in the performance analysis time period were in the target $SpO_2$ range; and
   an eupoxic time duration, in which the input $SpO_2$ values in the performance analysis time period were in the target $SpO_2$ range, or above the target $SpO_2$ range in room air.

7. The method of claim 1, wherein:
   the immediate control values are generated by multiplying error values by the immediate gain coefficient, wherein the error values are associated with differences between the input $SpO_2$ values and the target $SpO_2$ value;
   the accumulation control values are generated by multiplying summation or integrals of the error values by the accumulation gain coefficient,
   the predictive control values are generated by multiplying differences or derivatives of the error values by the predictive gain coefficient.

8. The method of claim 1, further including:
   determining, by the controlling apparatus, a target $SpO_2$ range, wherein the target $SpO_2$ is within the target $SpO_2$ range;
   wherein, when a current input $SpO_2$ value is within the target $SpO_2$ range, an attenuator is applied to the immediate control value, the attenuator being generated based on the current input $SpO_2$ value and a midpoint of the target $SpO_2$ range.

9. The method of claim 1, wherein, when a current input $SpO_2$ value is lower than the target $SpO_2$ value, an error value associated with a difference between the current input $SpO_2$ value and the target $SpO_2$ value is capped at a selected maximum error value.

10. The method of claim 1, wherein generating the accumulation control values includes:
    inhibiting increases in the accumulation control values when: (i) a current output $FiO_2$ value is at room air level, and (ii) a current input $SpO_2$ value is above the target $SpO_2$ value.

11. The method of claim 1, wherein the predictive control values are nullified if the input $SpO_2$ values have been above a selected $SpO_2$ threshold for a $SpO_2$ slope determination period.

12. The method of claim 1, further including:
    generating, by the controlling apparatus, an $rFiO_2$ evaluation result based on the input $SpO_2$ values and the respective output $FiO_2$ values over an $rFiO_2$ evaluation time period; and
    modifying, by the controlling apparatus, the $rFiO_2$ value based on the $rFiO_2$ evaluation result.

13. The method of claim 1, further including:
generating, by the controlling apparatus, a $SpO_2$ validation result based on a current input $SpO_2$ value by classifying the current input $SpO_2$ value into one of multiple validity levels in a hierarchical validation procedure; and
determining, by the controlling apparatus, the output $FiO_2$ value based on the $SpO_2$ validation result.

14. The method of claim 1, further including:
receiving, by the controlling apparatus, manual override input;
determining, by the controlling apparatus, the output $FiO_2$ value based on the manual override input instead of the control values.

15. The method of claim 1, wherein the immediate gain coefficient has an initial value between −2 and −0.2.

16. The method of claim 1, wherein the accumulation gain coefficient has an initial value between −0.25 and −0.005.

17. The method of claim 1, wherein the predictive gain coefficient has an initial value between −2 and −0.25.

18. The method of claim 1, wherein the immediate gain coefficient has an initial value being −1.

19. The method of claim 1, wherein the accumulation gain coefficient has an initial value being −0.0125.

20. The method of claim 1, wherein the predictive gain coefficient has an initial value being −1.

21. An apparatus for automatically controlling inspired oxygen delivery, including:
an input unit, receiving signals representing a plurality of input oxygen saturation ($SpO_2$) values for a patient;
a memory, recording the received input $SpO_2$ values;
a controller, determining output inspired oxygen concentration ($FiO_2$) values based on the input $SpO_2$ values; and
an output unit, outputting the determined output $FiO_2$ values;
wherein the controller:
generates control values based on the input $SpO_2$ values and a target $SpO_2$ value; and
generates the output inspired oxygen concentration ($FiO_2$) values based on the control values and reference inspired oxygen concentration ($rFiO_2$) values;
wherein the control values include:
immediate control values, generated based on the input $SpO_2$ values, the target $SpO_2$ value, and an immediate gain coefficient;
accumulation control values, generated based on the input $SpO_2$ values, the target $SpO_2$ value, and an accumulation gain coefficient; and
predictive control values, generated based on the input $SpO_2$ values, the target $SpO_2$ value, and a predictive gain coefficient;
wherein the immediate control values are determined based on the $rFiO_2$ value; and
wherein a non-linear compensation weighting is applied to the accumulation control value based on a predetermined non-linear relationship between partial pressure of arterial oxygen ($PaO_2$) and $SpO_2$.

22. A system for automatically controlling inspired oxygen delivery, including:
one or a plurality of oxygen saturation monitoring devices, and one or a plurality of inspired oxygen control devices;
a controlling device; and
a network, enabling communication between the one or a plurality of oxygen saturation monitoring devices and the controlling device, and communication between the one or a plurality of inspired oxygen control devices and the controlling device,
wherein the controlling device controls inspired oxygen delivery by:
receiving signals representing a plurality of input oxygen saturation ($SpO_2$) values for a patient from each of the one or a plurality of oxygen saturation monitoring devices through the network;
generating control values based on the input $SpO_2$ values and a target $SpO_2$ value;
generating output inspired oxygen concentration ($FiO_2$) values based on the control values and reference inspired oxygen concentration ($rFiO_2$) values;
sending the determined output $FiO_2$ values to a corresponding inspired oxygen control device through the network;
wherein the control values include:
immediate control values, generated based on the input $SpO_2$ values, the target $SpO_2$ value, and an immediate gain coefficient;
accumulation control values, generated based on the input $SpO_2$ values, the target $SpO_2$ value, and an accumulation gain coefficient; and
predictive control values, generated based on the input $SpO_2$ values, the target $SpO_2$ value, and a predictive gain coefficient;
wherein the immediate control values are determined based on the $rFiO_2$ value; and
wherein a non-linear compensation weighting is applied to the accumulation control value based on a predetermined non-linear relationship between partial pressure of arterial oxygen ($PaO_2$) and $SpO_2$.

* * * * *